(12) United States Patent
Dervieux et al.

(10) Patent No.: US 11,761,965 B2
(45) Date of Patent: *Sep. 19, 2023

(54) METHODS FOR DIAGNOSING SYSTEMIC LUPUS ERYTHEMATOSUS

(71) Applicant: Exagen Inc., Vista, CA (US)

(72) Inventors: Thierry Dervieux, San Diego, CA (US); Cole Harris, Houston, TX (US)

(73) Assignee: EXAGEN INC., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,229

(22) Filed: Feb. 15, 2023

(65) Prior Publication Data

US 2023/0194548 A1      Jun. 22, 2023

Related U.S. Application Data

(63) Continuation of application No. 17/743,289, filed on May 12, 2022, which is a continuation of application No. 16/135,694, filed on Sep. 19, 2018, now Pat. No. 11,360,099, which is a continuation of application No. 13/992,086, filed as application No. PCT/US2012/024729 on Feb. 10, 2012, now Pat. No. 10,132,813.

(60) Provisional application No. 61/472,424, filed on Apr. 6, 2011, provisional application No. 61/442,454, filed on Feb. 14, 2011, provisional application No. 61/441,785, filed on Feb. 11, 2011.

(51) Int. Cl.
| | |
|---|---|
| *G01N 33/53* | (2006.01) |
| *G01N 33/68* | (2006.01) |
| *G01N 33/564* | (2006.01) |

(52) U.S. Cl.
CPC ....... *G01N 33/6854* (2013.01); *G01N 33/564* (2013.01); *G01N 2800/104* (2013.01); *G01N 2800/56* (2013.01)

(58) Field of Classification Search
None
See application file for complete search history.

(56) References Cited

U.S. PATENT DOCUMENTS

| | | |
|---|---|---|
| 7,361,517 B2 | 4/2008 | Ahearn et al. |
| 7,390,631 B2 | 6/2008 | Ahearn et al. |
| 7,585,640 B2 | 9/2009 | Ahearn et al. |
| 7,588,905 B2 | 9/2009 | Ahearn et al. |
| 8,080,382 B2 | 12/2011 | Ahearn et al. |
| 8,126,654 B2 | 2/2012 | Ahearn et al. |
| 9,804,156 B2 | 10/2017 | Ramachandran et al. |
| 10,132,813 B2 * | 11/2018 | Dervieux ........... G01N 33/6854 |
| 11,360,099 B2 * | 6/2022 | Dervieux ........... G01N 33/6854 |
| 11,531,033 B2 | 12/2022 | Dervieux et al. |
| 2006/0071797 A1 | 4/2006 | Rosenfeld et al. |
| 2007/0148704 A1 | 6/2007 | Klause et al. |
| 2010/0233752 A1 | 9/2010 | Ahearn et al. |
| 2011/0177531 A1 | 7/2011 | Dervieux et al. |
| 2015/0369824 A1 | 12/2015 | Dervieux et al. |
| 2022/0276259 A1 | 9/2022 | Dervieux et al. |

FOREIGN PATENT DOCUMENTS

| | | |
|---|---|---|
| EP | 2 336 769 A1 | 6/2011 |
| WO | WO-2007/039280 A1 | 4/2007 |
| WO | WO-2007/117141 A1 | 10/2007 |
| WO | WO-2010/045611 A2 | 4/2010 |
| WO | WO-2010/045611 A3 | 4/2010 |
| WO | WO-2011/047337 A2 | 4/2011 |
| WO | WO-2011/047337 A3 | 4/2011 |
| WO | WO-2014/151238 A1 | 9/2014 |

OTHER PUBLICATIONS

Aarden, L.A. et al. (1975). "Immunology of DNA. III. *Crithidia Luciliae*, a Simple Substrate for the Determination of Anti-dsDNA with the Immunofluorescence Teqnique," *N.Y. Annal. Acad. Sci.* 254:505-515.

Amissah-Arthur, M.B. et al. (Jul. 2010). "Contemporary treatment of systemic lupus erythematosus: an update for clinicians," *Ther Adv Chronic Dis* 1(4):163-175.

Bang, H. et al. (Aug. 2007). "Mutation and citrullination modifies vimentin to a novel autoantigen for rheumatoid arthritis," *Arthritis Rheum* 56(8):2503-2511.

Bastian, H.M. et al. (2002). "Systemic lupus erythematosus n three ethnic groups. XII. Risk factors for lupus nephritis after diagnosis," *Lupus* 11(3):152-160.

Batal,I, et al. (Jan. 2012, e-published Sep. 29, 2011). "Prospective assessment of C4d deposits on circulating cells and renal tissues in lupus nephritis: a pilot study," *Lupus* 21(1):13-26.

Clough, J.D. et al. (Feb. 1984). "Weighted criteria for the diagnosis of systemic lupus erythematosus," *Arch Intern Med* 144(2):281-285.

Costenbader, K.H. et al. (Dec. 2002). "Defining lupus cases for clinical studies: the Boston weighted criteria for the classification of systemic lupus erythematosus," *J Rheumatol* 29(12)2545-2550.

Durcan, L. et al. (Nov. 2015, e-published Oct. 1, 2015). "Hydroxychloroquine Blood Levels in Systemic Lupus Erythematosus: Clarifying Dosing Controversies and Improving Adherence," *J Rheumatol* 42(11):2092-2097.

Egner, W. (Jun. 2000). "The use of laboratory tests in the diagnosis of SLE," *J Clin Pathol* 53(6):424-432.

Helmick, C.G. et al. (Jan. 2008). "Estimates of the prevalence of arthritis and other rheumatic conditions in the United States. Part I," *Arthritis Rheum* 58(1):15-25.

Hosmer, D.W. et al. (Apr. 2013). Applied Logistic Regression, 3rd Edition, 518 pages.

International Search Report dated Aug. 1, 2014, for PCT Application No. PCT/US2014/025264, filed Mar. 13, 2014, 5 pages.

(Continued)

*Primary Examiner* — Gary Counts
(74) *Attorney, Agent, or Firm* — Mintz, Levin, Cohn, Ferris, Glovsky and Popeo, P.C.

(57) ABSTRACT

The present invention provides methods of diagnosing and monitoring systemic lupus erythematosus.

9 Claims, 15 Drawing Sheets

(56) References Cited

OTHER PUBLICATIONS

Kalunian, K.C. et al., (Dec. 2012). "Measurement of cell-bound complement activation products enhances diagnostic performance in systemic lupus erythematosus," *Arthritis & Rheumatism* 64(12):4040-4047.

Kao A.H. et al. (Mar. 2010). "Erythrocyte C3d and C4d for monitoring lisease activity in systemic lupus erythematosus," *Arthritis and Rheumatism* 62(3):837-844.

Manderson, A.P. et al. (2004). "The role of complement in the development of systemic lupus erythematosus," *Annu Rev Immunol* 22:431-456.

Mok, C.C. et al. (Sep. 2016, e-published Jul. 27, 2016). "Hydroxychloroquine Serum Concentrations and Flares of Systemic Lupus Erythematosus: a Longitudinal Cohort Analysis," *Arthritis Care Res* 68(9):1295-1302.

Navratil, J.S. et al. (Feb. 2006). "Platelet C4d is highly specific for systemic lupus erythematosus," *Arthritis Rheum* 54(2):670-674.

Park, H.A. (Apr. 2013). An introduction to logistic regression: from basic concepts to interpretation with particular attention to nursing domain, *J Korean Acad Nurs* 43(2):154-164.

Petri, M.A. et al. (Mar. 30, 2019). "Platelet-bound C4d, low C3 and lupus anticoagulant associate with thrombosis in SLE," *Lupus Sci Med* 6(1):e000318.

Poulsom, H. et al. (2008). "Antibodies to Citrullinated Vimentin are a Specific and Sensitive Marker for the Diagnosis of Rheumatoid Arthritis," *Clinic Rev Aller Immunol*, 34:4-10.

Putterman, C. et al. (Oct. 2013). "An Assay Panel Combining Cell Bound Complement Activation Products With Autoantibodies to Extractable Nuclear Antigens and Mutated Citrullinated Vimentin Helps with the Differential Diagnosis of Systemic Lupus Erythematosus," *Arthritis & Rheumatism* 65(S10):S1078.

Putterman, C. et al. (Dec. 3, 2013). "Multicenter study in the "an Assay Panel Combining Cell Bound Complement Activation Products with Autoantibodies to Extractable Nuclear Antigens and Mutated Citrullinated Vimentin Helps with the Differential Diagnosis of Systemic Lupus Erythematosus," 2013 ACR/ARHP Annual Meeting, 5 pages.

Putterman, C. et al. (Oct. 1, 2014). "Cell-bound complement activation products in systemic lupus erythematosus: comparison with anti-double-stranded DNA and standard complement measurements," *Lupus Sci Med* 1(1):e000056.

Rahman, A. et al. (Feb. 28, 2008). "Systemic lupus erythematosus," *N Engl J Med* 358(9):929-939.

Singh, V. et al. (Oct. 2008, e-published Aug. 15, 2008). "Erythrocyte C4d and complement receptor 1 in systemic lupus erythematosus," *J Rheumatol* 35(10):1989-1993.

Smith, E.L. et al. (1999). "The American College of Rheumatology criteria for the classification of systemic lupus erythematosus: strengths, weaknesses, and opportunities for improvement," *Lupus* 8(8):586-595.

Sperandei, S. et al. (2014). "Undersanding Logistic Regression Analysis," Biochemia Medica 24(1):12-18.

Tan, E.M. et al. (Nov. 1982). "The 1982 revised criteria for the classification pf systemic lupus erythematosus," *Arthritis Rheum* 25(11):1271-1277.

Written Opinion dated Aug. 1, 2014, for PCT Application No. PCT/US2014/025264, filed Mar. 13, 2014, 6 pages, 2014.

Yang, D.H. et al. (Sep. 2009, e-published Jun. 24, 2009). "Usefulness of erythrocyte-bound C4d as a biomarker to predict lisease activity in patients with systemic lupus erythemastosus," *Rheumatology (Oxford)* 48(9):1083-1087.

International Search Report for PCT/U.S. Pat. No. 20121024729, dated Jul. 25, 2012.

Hullo, et al. (2009), "Citrullinated antibodies in systemic lupus erythematosus and primary Sjogren's syndrome," 2nd European Congress of Immunology, abstract PC14/48.

Liu, et al., (2009), "Lymphocyte-bound complement activation products as biomarkers for diagnosis of systemic lupus erythematosus," Clinical and Translational Science, 2(4):300-308.

Kalunian, et al., (2011) "The contribution of cell bound complement activation products to the diagnosis of Systemic Lupus Erythematosus," Arthritis & Rheumatism, 63: 1-2, abstract supplement.

Manzi, et al., (2004) "New insights into complement: a mediator of injury and marker of disease activity in systemic lupus erythematosus," Lupus, 13:298-303.

Corvetta, et al., (1991) "Low Number of complement C3b/C4b receptors (CR) erythrocytes from patients with essential—mixed cryglobulinemia, systemic lupus erythematosus and rheumatoid arthritis: relationship with disease activity anticardolipin antibodies, complement activation and therapy," J. Rheumatol, 18:1021.

Ross, et al. (1985) "Disease-associated loss of erythrocyte complement receptors CR1, C3b receptors) in patients with systemic lupus erythematosus and other diseases involving autoantibodies and/or complement activation," J. Immunol, 135:2005.

Iida, et al., "Complement receptor (CR1) deficiency in erythrocytes from patients with systemic lupus mythematosus," J. Exp. Med, 155:1427-1438, May 1982.

Manzi et al., Measurement of erythorycte C4d and complement receptor 1 in systemic lupus erythemastosus, Arthritis and Rheumatism 2004; vol. 50 p. 3596-3604.

Petri et al., Classification criteria for systemic lupus erythematosus: a reivew, Lupus 2004, vol. 13, pp. 829-837.

* cited by examiner

FIG. 3
FIG. 3A
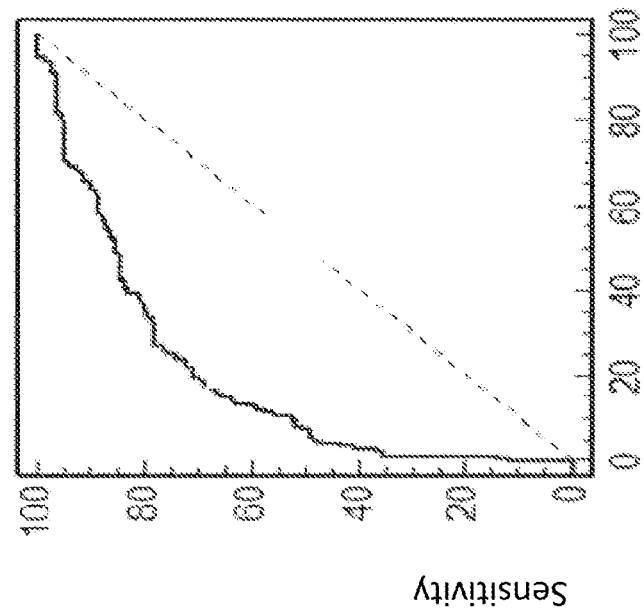
FIG. 3B
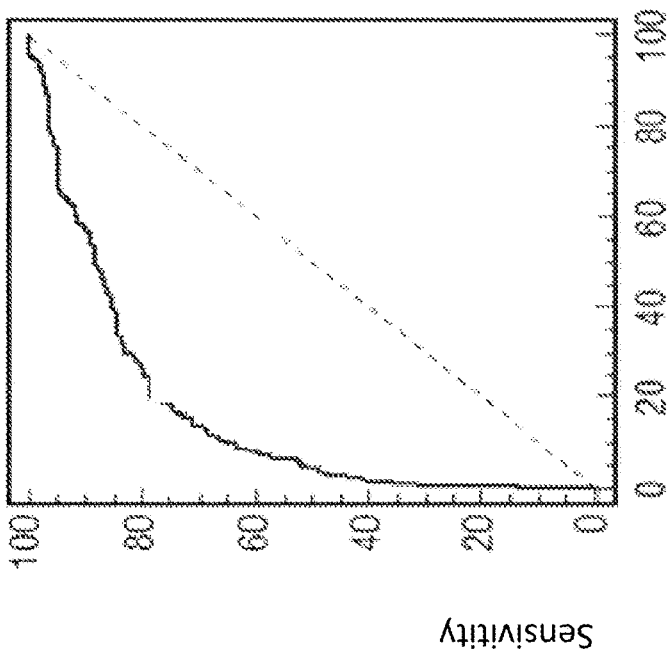

| | Test Result |
|---|---|
| ANA | Positive |
| dsDNA | Negative |
| AntiMCV | Negative |
| EC4D | 37 Net MFI |
| BC4D | 102 Net MFI |

| | Test Result |
|---|---|
| Index | 4.19 |
| Probability of SLE | 98.5% |

METHODS FOR DIAGNOSING SYSTEMIC LUPUS ERYTHEMATOSUS

CROSS-REFERENCE TO RELATED APPLICATIONS

This application is a continuation of U.S. application Ser. No. 17/743,289 filed May 12, 2022, which is a continuation of U.S. application Ser. No. 16/135,694 filed Sep. 19, 2018, issued as U.S. Pat. No. 11,360,099, which is a continuation of U.S. application Ser. No. 13/992,086 filed Jul. 2, 2013, issued as U.S. Pat. No. 10,132,813, which is a Section 371 US National Phase of International Application No. PCT/US2012/024729 filed Feb. 10, 2012, which claims priority to U.S. Application No. 61/441,785 filed Feb. 11, 2011, U.S. Application No. 61/442,454 filed Feb. 14, 2011, and U.S. Application No. 61/472,424 filed Apr. 6, 2011, all of which are incorporated by reference herein in their entirety.

BACKGROUND OF THE INVENTION

Systemic lupus erythematosus (SLE) is an autoimmune disease, characterized by the production of unusual autoantibodies in the blood. These autoantibodies bind to their respective antigens, forming immune complexes which circulate and eventually deposit in tissues. This immune complex deposition causes chronic inflammation and tissue damage.

The precise reason for the abnormal autoimmunity that causes lupus is not known. Inherited genes, viruses, ultraviolet light, and drugs may all play some role. Genetic factors increase the tendency of developing autoimmune diseases, and autoimmune diseases such as lupus, rheumatoid arthritis, and immune thyroid disorders are more common among relatives of patients with lupus than the general population. Some scientists believe that the immune system in lupus is more easily stimulated by external factors like viruses or ultraviolet light. Sometimes, symptoms of lupus can be precipitated or aggravated by only a brief period of sun exposure.

Since patients with SLE can have a wide variety of symptoms and different combinations of organ involvement, no single test establishes the diagnosis of SLE. To help doctors improve the accuracy of diagnosis of SLE, eleven criteria were established by the American Rheumatism Association. These eleven criteria are closely related to the variety of symptoms observed in patients with SLE. When a person has four or more of these criteria, the diagnosis of SLE is strongly suggested. However, some patients suspected of having SLE may never develop enough criteria for a definite diagnosis. Other patients accumulate enough criteria only after months or years of observation. Nevertheless, the diagnosis of SLE may be made in some settings in patients with only a few of these classical criteria. Of these patients, a number may later develop other criteria, but many never do. The eleven criteria conventionally used for diagnosing SLE are: (1) malar over the cheeks of the face or "butterfly" rash; (2) discoid skin rash: patchy redness that can cause scarring; (3) photosensitivity: skin rash in reaction to sunlight exposure; (4) mucus membrane ulcers: ulcers of the lining of the mouth, nose or throat; (5) arthritis: two or more swollen, tender joints of the extremities; (6) pleuritis/pericarditis: inflammation of the lining tissue around the heart or lungs, usually associated with chest pain with breathing; (7) kidney abnormalities: abnormal amounts of urine protein or clumps of cellular elements called casts; (8) brain irritation: manifested by seizures (convulsions) and/or psychosis; (9) blood count abnormalities: low counts of white or red blood cells, or platelets; (10) immunologic disorder: abnormal immune tests include anti-dsDNA or anti-Sm (Smith) antibodies, false positive blood tests for syphilis, anticardiolipin antibodies, lupus anticoagulant, or positive LE prep test, and (11) antinuclear antibody: positive ANA antibody testing.

Although the criteria serve as useful reminders of those features that distinguish lupus from other related autoimmune diseases, they are unavoidably fallible. Determining the presence or absence of the criteria often requires interpretation. If liberal standards are applied for determining the presence or absence of a sign or symptom, one could easily diagnose a patient as having lupus when in fact they do not. Similarly, the range of clinical manifestations in SLE is much greater than that described by the eleven criteria and each manifestation can vary in the level of activity and severity from one patient to another. To further complicate a difficult diagnosis, symptoms of SLE continually evolve over the course of the disease. New symptoms in previously unaffected organs can develop over time. Because conventionally there is no definitive test for lupus, it is often misdiagnosed.

Monitoring disease activity is also problematic in caring for patients with lupus. Lupus progresses in a series of flares, or periods of acute illness, followed by remissions. The symptoms of a flare, which vary considerably between patients and even within the same patient, include malaise, fever, symmetric joint pain, and photosensitivity (development of rashes after brief sun exposure). Other symptoms of lupus include hair loss, ulcers of mucous membranes and inflammation of the lining of the heart and lungs which leads to chest pain.

Red blood cells, platelets and white blood cells can be targeted in lupus, resulting in anemia and bleeding problems. More seriously, immune complex deposition and chronic inflammation in the blood vessels can lead to kidney involvement and occasionally failure requiring dialysis or kidney transplantation. Since the blood vessel is a major target of the autoimmune response in lupus, premature strokes and heart disease are not uncommon. Over time, however, these flares can lead to irreversible organ damage. In order to minimize such damage, earlier and more accurate detection of disease flares would not only expedite appropriate treatment, but would reduce the frequency of unnecessary interventions. From an investigative standpoint, the ability to uniformly describe the "extent of inflammation" or activity of disease in individual organ systems or as a general measure is an invaluable research tool. Furthermore, a measure of disease activity can be used as a response variable in a therapeutic trial.

SUMMARY OF THE INVENTION

In a first aspect, the present invention provides methods for diagnosing systemic lupus erythematosus (SLE), or monitoring SLE disease activity comprising: (a) determining the level of at least one marker selected from the group consisting of BC4d (B-lymphocyte-bound C4d), EC4d (erythrocyte-bound C4d), PC4d (platelet-bound C4d), and ECR1 (erythrocyte complement receptor type 1) in a biological sample from the subject; (b) determining the level of at least one further marker in a biological sample from the subject selected from the group consisting of anti-MCV antibody marker and anti-nuclear antibody (ANA) marker; (c) calculating an SLE risk score by adjusting the level of one or more of the markers by one or more transformation analyses; (d) comparing the SLE risk score to a standard; and (e) one or more of: (I) diagnosing the subject as having SLE based on the comparison; (II) determining a level of SLE disease activity based on the comparison; (III) providing the comparison to an entity for diagnosis of SLE; and (IV) providing the comparison to an entity for monitoring SLE disease activity.

In one embodiment, steps (a) and (b) comprise determining a level of (a) EC4d marker and BC4d marker in a biological sample from a subject; and (b) one or both of anti-MCV antibody marker and anti-nuclear antibody (ANA) marker in a biological sample from the subject. In one embodiment, the method comprises determining a level of both the anti-MCV and the ANA markers. In another embodiment, step (a) further comprises determining a level of ECR1 in a biological sample from the subject.

In another embodiment, steps (a) and (b) comprise determining a level of (a) ECR1 and PC4d in a biological sample from a subject; and (b) ANA marker in a biological sample from the subject.

In another embodiment, steps (a) and (b) comprise determining a level of (a) EC4d, BC4d, PC4d, and ECR1 in a biological sample from a subject; and (b) ANA marker in a biological sample from the subject. This embodiment may further comprise determining a level of anti-MCV antibody marker in a biological sample from the subject.

In another embodiment of any of the above embodiments, or combinations thereof, the method further comprises determining a level of double stranded DNA antibody (anti-dsDNA) marker in a biological sample from the subject. In a further embodiment, determining the level of double stranded DNA antibody (anti-dsDNA) marker in the biological sample is carried out prior to determining the level of the other markers.

In various embodiments of any of the above embodiments, step (a) comprises determining a level of 2, 3, or all 4 of the recited markers in a biological sample from the subject.

In another embodiment, the one or more transformation analyses comprises logistic regression analysis, and wherein the logistic regression analysis comprises (i) adjusting the level of one or more of the markers by an appropriate weighting coefficient to produce a weighted score for each marker, and (ii) combining the weighted score for each marker to generate the SLE risk score. In a further embodiment, the level of 2, 3, 4, 5, or all markers is adjusted.

In yet another embodiment, calculating the SLE risk score comprises: (i) multiplying the amount of the markers by a predetermined weighting coefficient to produce the weighted score for each marker; and (ii) summing the individual weighted scores to produce the SLE risk score.

In one embodiment, the biological sample comprises a blood sample. In another embodiment, determining the BC4d marker level comprises determining the level of BC4d on the surface of B lymphocytes, determining the PC4d marker level comprises determining the level of PC4d on the surface of platelets, and/or determining the EC4d and/or ECR1 marker level comprises determining the level of EC4d and/or ECR1 on the surface of erythrocytes. In a further embodiment, determining the BC4d marker level comprises determining the level of BC4d in a cell or tissue extract comprising B lymphocytes, determining the PC4d marker level comprises determining the level of PC4d in a cell or tissue extract comprises platelets, and/or determining the EC4d and/or ECR1 marker level comprises determining the level of EC4d and/or ECR1 in a cell or tissue extract comprising erythrocytes. In a still further embodiment, the level of the BC4d marker, the level of the PC4d marker, and/or the level of the EC4d marker is determined using an antibody specific for C4d.

The methods may further comprise contacting the biological sample with IgM, IgG and/or IgA rheumatoid factors, and/or anti-CCP antibodies under conditions suitable to promote specific binding of the antibodies to their target antigen in the biological sample, removing unbound antibodies, detecting binding complexes between the antibodies and their targets in the biological sample, and comparing a level of such binding complexes to a standard, wherein an increase in such binding complexes relative to the standard indicates that the subject has rheumatoid arthritis.

In one embodiment, the method comprises providing the comparison to an entity for diagnosis of SLE. In another embodiment, the method comprises providing the comparison to an entity for monitoring SLE disease activity. In a further embodiment, the method comprises diagnosing the subject as having SLE based on the comparison. In another embodiment, the method comprises determining a level of SLE disease activity based on the comparison.

In a second aspect, the present invention provides methods for diagnosing systemic lupus erythematosus (SLE) comprising (a) determining a level of double stranded DNA antibodies (anti-dsDNA), in a biological sample from a subject; (b) determining a level of at least one marker selected from the group consisting of BC4d (B-lymphocyte-bound C4d), EC4d (erythrocyte-bound C4d), PC4d (platelet-bound C4d), and ECR1 (erythrocyte complement receptor type 1) in a biological sample from the subject; (c) calculating an SLE risk score by adjusting the level of one or more of the markers by one or more transformation analyses; (d) comparing the SLE risk score to a standard; and (e) one or more of: (I) diagnosing the subject as having SLE based on the comparison; (II) determining a level of SLE disease activity based on the comparison; (III) providing the comparison to an entity for diagnosis of SLE; and (IV) providing the comparison to an entity for monitoring SLE disease activity.

In one embodiment, the method comprises determining the level of double stranded DNA antibody (anti-dsDNA) marker in the biological sample prior to determining the level of the one or more other markers in step (b). In various embodiments of any of the above embodiments, step (b) comprises determining a level of 2, 3, or all 4 of the recited markers in a biological sample from the subject.

In another embodiment, the one or more transformation analyses comprises logistic regression analysis, and wherein the logistic regression analysis comprises (i) adjusting the level of one or more of the markers by an appropriate weighting coefficient to produce a weighted score for each marker, and (ii) combining the weighted score for each marker to generate the SLE risk score. In a further embodiment, the level of all markers is adjusted.

In another embodiment, calculating the SLE risk score comprises (i) multiplying the amount of the markers by a predetermined weighting coefficient to produce the weighted score for each marker; and (ii) summing the individual weighted scores to produce the SLE risk score.

In one embodiment, the sample is a blood sample. In another embodiment, determining the BC4d marker level comprises determining the level of BC4d on the surface of B lymphocytes, determining the level of PC4d on the surface of B lymphocytes comprises determining the level of BC4d on the surface of platelets, and/or determining the EC4d and/or ECR1 marker level comprises determining the level of EC4d and/or ECR1 on the surface of erythrocytes. In a further embodiment, determining the BC4d marker level comprises determining the level of BC4d in a cell or tissue extract comprising B lymphocytes, determining the PC4d marker level comprises determining the level of PC4d in a cell or tissue extract comprising platelets, and/or determining the EC4d and/or ECR1 marker level comprises determining the level of EC4d and/or ECR1 in a cell or tissue extract comprising erythrocytes.

In another embodiment, the level of the BC4d marker, the PC4d, and/or the level of the EC4d marker is determined using an antibody specific for C4d. In a further embodiment, the methods further comprise contacting the biological sample with ANA, anti-MCV, IgG and/or IgA rheumatoid factors, and/or anti-CCP antibodies under conditions suitable to promote specific binding of the antibodies to their target antigen in the biological sample, removing unbound antibodies, detecting binding complexes between the antibodies and their targets in the biological sample, and comparing a level of such binding complexes to a standard, wherein an increase in such binding complexes relative to the standard indicates that the subject has rheumatoid arthritis.

In one embodiment, the method comprises providing the comparison to an entity for diagnosis of SLE. In another embodiment, the method comprises providing the comparison to an entity for monitoring SLE disease activity. In a further embodiment, the method comprises diagnosing the subject as having SLE based on the comparison. In another embodiment, the method comprises determining a level of SLE disease activity based on the comparison.

In a third aspect, the present invention provides a non-transitory computer readable storage medium comprising a set of instructions for causing a device for measuring marker levels in a biological sample to carry out the method of any of the embodiment or combination of embodiments of the methods of the inventions.

In a fourth aspect, the present invention provides a combination of tests comprising at least three of: (a) a first test for the level of EC4d; (b) a second test for the level of BC4d; (c) a third test for the level of anti-MCV antibodies; (d) a fourth test for the level of ANA; and (e) a fifth test for the level of anti-dsDNA antibodies.

BRIEF DESCRIPTION OF THE DRAWINGS

FIGS. 3A-3B are graphs demonstrating discriminating power of the EC4D marker. FIG. 3A: SLE vs. all others: area 0.846; sensitivity 76.4, specificity 80.3; criterion >7.15. FIG. 3B: SLE vs. other diseases: area 0.814; sensitivity: 69.0; specificity: 82.7; criterion: >8.94.

FIG. 4A: SLE vs. all others: area 0.701; sensitivity 73.7, specificity 59.2; criterion ≤16.25. FIG. 4B: SLE vs. other diseases: area 0.619; sensitivity: 47.6; specificity: 64.5; criterion: ≤16.25.

FIG. 5A: SLE vs. all others: area 0.847; sensitivity 70.9, specificity 84.3; criterion >39.385.

FIG. 5B: SLE vs. other diseases: area 0.806; sensitivity: 65.7; specificity: 83.0; criterion: >43.55.

DETAILED DESCRIPTION OF THE INVENTION

Figure 1:
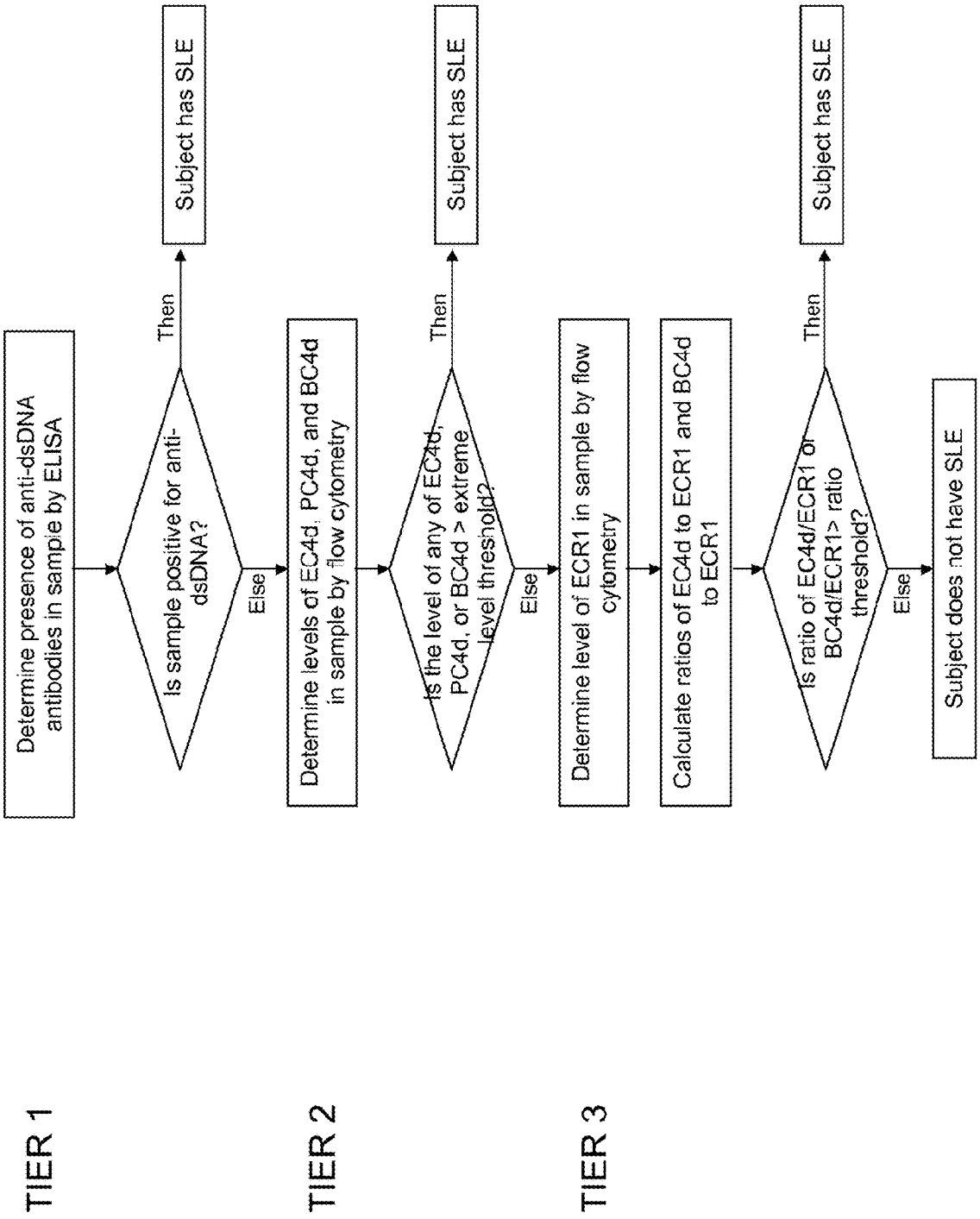
FIG. 1 is a flow chart illustrating an embodiment of the methods of the invention for diagnosing SLE based on blood sample levels of cell-based complement activation products containing three detection tiers.

All references cited are herein incorporated by reference in their entirety.

Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, $2^{nd}$ Ed. (R. I. Freshney. 1987. Liss, Inc. New York, NY), Gene Transfer and Expression Protocols, pp. 109-128, ed. E. J. Murray, The Humana Press Inc., Clifton, N.J.), and the Ambion 1998 Catalog (Ambion, Austin, TX).

All embodiments disclosed herein can be combined with one or more other embodiments in the same or different aspect of the invention, unless the context clearly indicates otherwise.

In a first aspect, the present invention provides methods for diagnosing systemic lupus erythematosus (SLE), or monitoring SLE disease activity comprising: (a) determining the level of at least one marker selected from the group consisting of BC4d (B-lymphocyte-bound C4d), EC4d (erythrocyte-bound C4d), PC4d (platelet-bound C4d), and ECR1 (erythrocyte complement receptor type 1) in a biological sample from the subject; (b) determining the level of at least one further marker in a biological sample from the subject selected from the group consisting of anti-MCV antibody marker and anti-nuclear antibody (ANA) marker;

(c) calculating an SLE risk score by adjusting the level of one or more of the markers by one or more transformation analyses; (d) comparing the SLE risk score to a standard; and (e) one or more of: (I) diagnosing the subject as having SLE based on the comparison; (II) determining a level of SLE disease activity based on the comparison; (III) providing the comparison to an entity for diagnosis of SLE; and (IV) providing the comparison to an entity for monitoring SLE disease activity.

The present invention provides methods for the diagnosis and monitoring of disease activity and response to treatment in systemic lupus erythematosus (SLE) using panels of biomarkers. The inventors demonstrate herein that the methods of the invention provide specificity and sensitivity of SLE diagnosis and disease monitoring compared to previous methods. For example, while the presence of anti-dsDNA antibodies has been used for diagnosing SLE and monitoring disease severity, there is a large subset of confirmed SLE patients (approximately 40-50%) that test negative for anti-dsDNA antibodies. Thus, traditional measures for diagnosing and monitoring SLE in a subject lack accuracy and sensitivity, and improved methods of diagnosis and monitoring are needed.

The subject may be any one at risk of SLE (in methods for diagnosing SLE), or one known to have SLE (in methods for monitoring disease activity), preferably a human subject (adult or pediatric). SLE is an autoimmune disease, characterized by the production of unusual autoantibodies in the blood. These autoantibodies bind to their respective antigens, forming immune complexes which circulate and eventually deposit in tissues. Symptoms of SLE include, but are not limited to, malaise, fever, chronic inflammation, tissue damage; malar over the cheeks of the face or "butterfly" rash; discoid skin rash: patchy redness that can cause scarring; photosensitivity: skin rash in reaction to sunlight exposure, mucus membrane ulcers: ulcers of the lining of the mouth, nose or throat; arthritis: two or more swollen, tender joints of the extremities; pleuritis/pericarditis: inflammation of the lining tissue around the heart or lungs, chest pain with breathing; hair loss; kidney abnormalities: abnormal amounts of urine protein or clumps of cellular elements called casts; brain irritation: manifested by seizures (convulsions) and/or psychosis; blood count abnormalities; immunologic disorder: abnormal immune tests include anti-dsDNA or anti-Sm (Smith) antibodies, false positive blood tests for syphilis, anticardiolipin antibodies, lupus anticoagulant, and positive LE prep test.

As used herein, the "biological sample" is obtained from the subject's body. Any suitable biological sample from the subject may be used. Particularly suitable samples for use in the methods of the invention are blood samples, biopsy samples, including but not limited to kidney biopsies. In one embodiment, serological markers (such as one or both of anti-MCV antibody marker and an ANA marker) are obtained from a blood sample, while EC4d, PC4d, ECR1, and/or BC4d markers are those deposited on circulating blood cells.

Blood samples are preferably treated with EDTA (ethylenediaminetetraacetate) to inhibit complement activation. Samples can be maintained at room temperature or stored at 4° C. In some embodiments, a whole blood sample may be fractionated into different components. For instance, in one embodiment, red blood cells are separated from other cell types in the sample by differential centrifugation. Analysis of complement activation products bound to erythrocytes (e.g., EC4d and ECR1) can be performed on the isolated red blood cells. In some embodiments, the white blood cells are isolated from other components of the blood sample. For example, white blood cells (the buffy coat) can be isolated from plasma and from red blood cells by centrifugation. Each type of white blood cell (e.g. lymphocyte, monocyte, etc.) can be isolated through the use of antibodies against known cell surface markers that are specific for that cell type. Antibodies against cell surface markers of white blood cells are known to those of skill in the art. For instance, monoclonal antibodies specific for cell surface markers CD3, CD4, CD8, and CD19 are commercially available and can be used to select lymphocytes. Analysis for complement activation products found on the surface of white blood cells, such as BC4d, can be performed in an isolated fraction of white blood cells. The platelet fraction can be from other blood components to allow analysis of platelet-bound complement activation products, such as PC4d. Platelet isolation can be performed with methods known in the art, including differential centrifugation or immunoprecipitation using antibodies specific for platelets (e.g., CD42b).

The level (e.g., quantity or amount) of a particular biomarker can be measured in the sample using a variety of methods known to those of skill in the art. Such methods include, but are not limited to, flow cytometry, ELISA using red blood cell, platelet, or white blood cell lysates (e.g., lymphocyte lysates), and radioimmunoassay. In one embodiment, the determination of the level of C4d is made using flow cytometric methods, with measurements taken by direct or indirect immunofluorescence using polyclonal or monoclonal antibodies specific for each of the molecules. Each of these molecules can be measured with a separate sample (e.g., red blood cell-, white blood cell-, or platelet-specific fractions) or using a single sample (e.g., whole blood).

In one embodiment, steps (a) and (b) comprise determining a level of (a) EC4d marker and BC4d marker in a biological sample from a subject; and (b) one or both of anti-MCV antibody marker and anti-nuclear antibody (ANA) marker in a biological sample from the subject. In one embodiment, the method comprises determining a level of both the anti-MCV and the ANA markers. In another embodiment, step (a) further comprises determining a level of ECR1 in a biological sample from the subject. This embodiment is described in detail in the examples that follow, and shows significant diagnostic improvement over prior art methods.

In another embodiment, steps (a) and (b) comprise determining a level of (a) ECR1 and PC4d in a biological sample from a subject; and (b) ANA marker in a biological sample from the subject. This embodiment is described in detail in the examples that follow, and shows significant diagnostic improvement over prior art methods.

In another embodiment, steps (a) and (b) comprise determining a level of (a) EC4d, BC4d, PC4d, and ECR1 in a biological sample from a subject; and (b) ANA marker in a biological sample from the subject. This embodiment may further comprise determining a level of anti-MCV antibody marker in a biological sample from the subject. This embodiment is described in detail in the examples that follow, and shows significant diagnostic improvement over prior art methods.

In various embodiments of any of the above embodiments, step (a) comprises determining a level of 2, 3, or all 4 of the recited markers in a biological sample from the subject.

In various embodiments of any of the above embodiments, step (b) comprises determining a level of both the anti-MCV and the ANA markers.

In another embodiment of any of the above embodiments, or combinations thereof, the method further comprises determining a level of double stranded DNA antibody (anti-dsDNA) marker in a biological sample from the subject. In a further embodiment, determining the level of double stranded DNA antibody (anti-dsDNA) marker in the biological sample is carried out prior to determining the level of the other markers.

In a further embodiment that can be combined with any methods disclosed herein, step the methods further comprise determining a level of double stranded DNA antibody (anti-dsDNA) marker in a biological sample from the subject. In this embodiment, the method may comprise determining the level of the (anti-dsDNA) marker in the biological sample prior to determining the level of the other markers.

Methods for determining levels of EC4d, BC4d, PC4d, ECR1, ANA, and anti-MCV are disclosed throughout (such as in the Examples that follow) and are known in the art, while methods for determining the level of anti-dsDNA are well known in the art, such as standard ELISAs. Any suitable assay for determining the level of the markers may be used, as discussed below. In one embodiment, determining the marker level comprises determining the level of BC4d on the surface of B lymphocytes, determining the level of PC4d on the surface of platelets, and/or determining the level of and/or ECR1 on the surface of erythrocytes. Suitable assays for making such determinations are known in the art and include methods described herein. In one embodiment, flow cytometry is used.

In another embodiment, determining the marker level comprises determining the level of BC4d in a cell or tissue extract comprising B lymphocytes, determining the level of PC4d in a cell or tissue extract comprising platelets, and/or determining the level of EC4d and/or ECR1 in a cell or tissue extract comprising erythrocytes. Suitable assays for making such determinations are known in the art, and include ELISA assays of relevant cell extracts using antibodies specific for C4d.

The methods or any embodiment or combination of embodiments herein may further comprise determining a ratio of one or more of EC4d and ECR1; BC4d and ECR1; and PC4d and ECR1. EC4D, PC4d, and BC4D tend to be elevated in SLE patients while ECR1 tends to be decreased. These ratios can be used in combination with the methods of the invention to help predict the likelihood of SLE. In one embodiment, the determination of the level of CR1 can be made using flow cytometric methods, with measurements taken by direct or indirect immunofluorescence using polyclonal or monoclonal antibodies specific for each of the molecules.

The methods described herein employ comparisons between a measured level of a biomarker and a standard. Any suitable standard for comparison can be used, including but not limited to a pre-determined level or range from a normal individual or population of subjects suffering from SLE, or as otherwise described herein. As used herein, a "pre-determined level" or "pre-determined range" refers to a value or range of values that can be determined from the quantity or amount (e.g., absolute value or concentration) of a particular biomarker measured in a population of control subjects (i.e. healthy subjects) or a population of subjects afflicted with an autoimmune disease such as SLE, or a non-SLE autoimmune disorder. A pre-determined level or pre-determined range can be selected by calculating the value or range of values that achieves the greatest statistical significance for a given set of amounts or quantities for a particular biomarker. In some embodiments, the pre-determined level can be based on the variance of a sample of biomarker quantities from a population of control/normal subjects. For instance, the pre-determined level can be at least 2, 3, 4, or 5 standard deviations above the normal range for a particular biomarker. In one embodiment, the pre-determined level is at least 6 standard deviations above the normal range for the biomarker. In some embodiments, a pre-determined level or pre-determined range can be a ratio of levels of two different biomarkers measured from all subjects (including SLE patients). A pre-determined level or pre-determined range can also be determined by calculating a level or range of biomarker quantities for which greater than 50%, 60%, 70%, 75%, 80%, 85%, 90%, or 95% of patients having a quantity of biomarker within that level or range have SLE. Samples in which the level of biomarker does not fall within the pre-determined range or pre-determined level, may require the measurement of an additional biomarker before a diagnosis of SLE can be made.

As used herein, "transformation analyses" can be any suitable mathematical operation, including but not limited to generalized models (e.g. logistic regression, generalized additive models), multivariate analysis (e.g. discriminant analysis, principal components analysis, factor analysis), and time-to-event "survival" analysis. In one preferred embodiment, the one or more transformation analyses comprises logistic regression analysis, and wherein the logistic regression analysis comprises (i) adjusting the level of one or more of the markers by an appropriate weighting coefficient to produce a weighted score for each marker, and (ii) combining the weighted score for each marker to generate the SLE risk score.

In various embodiments, the levels of one, two, three, four, five, or more (where additional markers used) markers may be adjusted by an appropriate weighting coefficient.

As will be understood by those of skill in the art based on the teachings herein, weighting coefficients can be determined by a variety of techniques and can vary widely. In one example of determining appropriate weighting coefficients, multivariable logistic regression (MLR) is performed using the maker levels found within two groups of patients, for example, one with and one without SLE. There are several methods for variable (marker) selection that can be used with MLR, whereby the markers not selected are eliminated from the model and the weighting coefficients for each predictive marker remaining in the model are determined. These weighting coefficients can then be, for example, multiplied by the marker level in the sample (expressed in any suitable units, including but not limited weight/volume, weight/weight, weight/number packed cells, etc.) and then, for example, summed to calculate an SLE risk score.

As used herein, "combining" includes any mathematical operation to use markers in combination to arrive at a single score that can be compared to a threshold (adding, subtracting, dividing, multiplying, and combinations thereof). In these methods, the level of 1, 2, 3, 4, 5, or all of the markers may be adjusted using an appropriate weighting coefficient. Preferably, all markers are adjusted.

In a further embodiment, calculating the SLE risk score comprises (i) multiplying the amount of the markers by a predetermined weighting coefficient to produce the weighted score for each marker; and (ii) summing the individual weighted scores to produce the SLE risk score.

Figure 14:
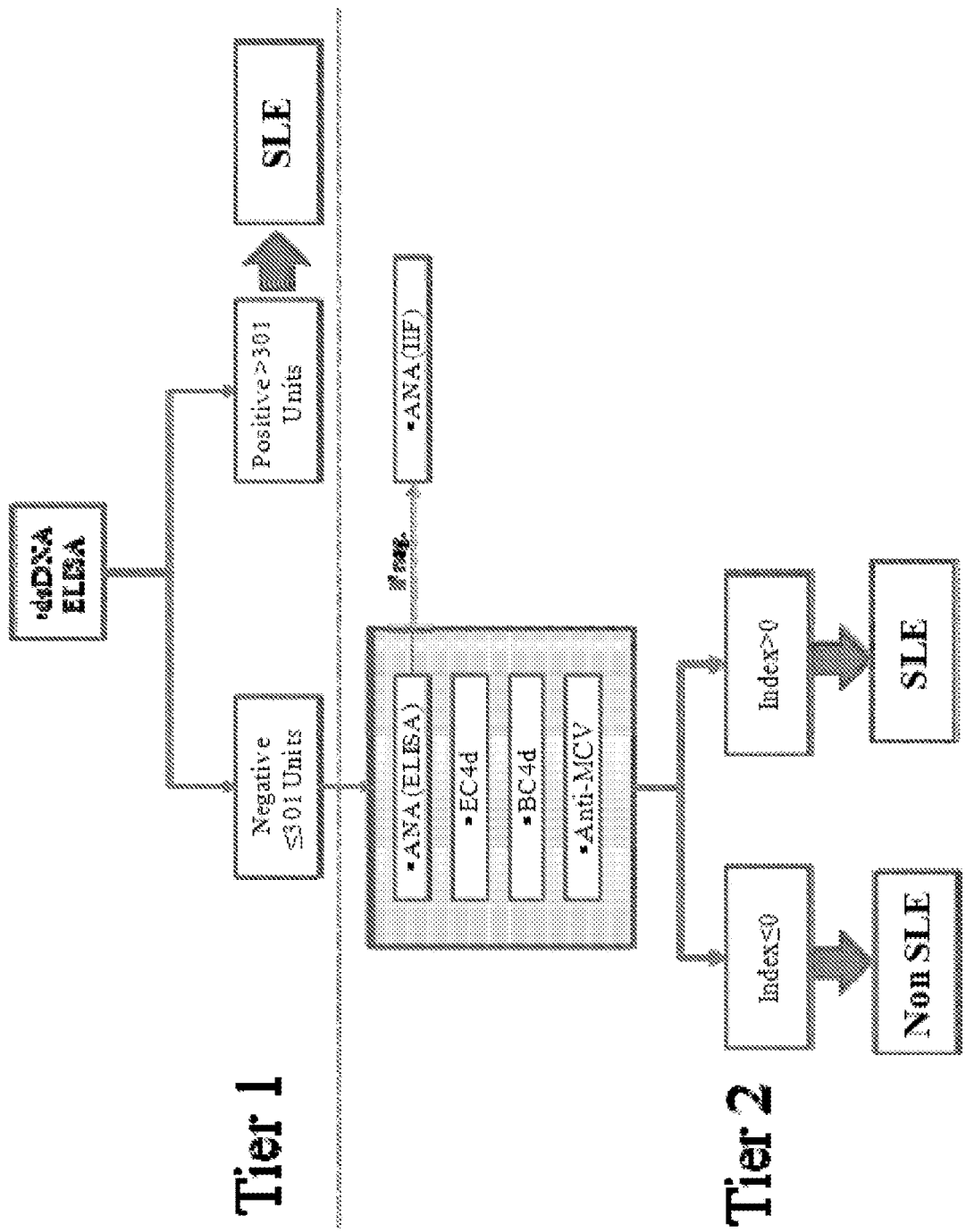
FIG. 14 is a flow chart illustrating an embodiment of the methods of the invention for diagnosing SLE based on marker levels containing two detection tiers.

In one embodiment, the methods comprise a single-tiered analysis, in which the risk factor is based on an index derived from a multivariate logistic regression equation, in which the presence or absence (or disease activity) of SLE is the classification variable and the markers are independent variables, one or more of them (1, 2, 3, 4, 5, all, etc.) associated with a coefficient. Examples of this embodiment are provided in the examples that follow. In other embodiments, the methods comprise a multi-tiered analysis. In one non-limiting embodiment, FIG. 14 illustrates a multi-tier analysis method. In Tier 1 positivity for dsDNA is associated with a diagnosis of SLE. Among dsDNA negative patients the index score composite of ANA, EC4d and BC4d levels measured by fluorescence-activated cell sorting (FACS) and anti-MCV (by ELISA) is calculated. An Index above a threshold is consistent with a diagnosis of SLE. In one embodiment, the index score is calculated using ANA determined by ELISA. In another embodiment, indirect immunofluorescence is performed when ANA is negative by ELISA.

In one embodiment, the methods may result in a diagnosis of the subject as having SLE based on the comparison. In another embodiment, the methods may result in providing the comparison to an entity for diagnosis of SLE. In these embodiments, the subject is at risk of SLE but has not been definitively diagnosed with SLE. In various embodiments, the subject may present with one or more symptoms of SLE, as described above. "Diagnosing/diagnosis," as used herein, means identifying the presence or nature of SLE. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

In another embodiment, the methods may result in determining a level of SLE disease activity based on the comparison. In a further embodiment, the methods may result in providing the comparison to an entity for monitoring SLE disease activity. In these embodiments, the methods can be used, for example, to differentiate between subjects with active disease and those with non-active disease, as demonstrated in the examples that follow. For example, as shown in the examples that follow, the risk scores can be used to differentiate SLE patients with active disease from those with non-active disease with high sensitivity and specificity.

In these embodiments, the subject is one known to have SLE the method is used to determine a course of disease. In one embodiment, the subject is being treated for SLE. Such treatment regimens may include, but are not limited to, immunosuppressants (ex: cyclophosphamide, corticosteroids, mycophenolate, etc.) and/or disease modifying anti-rheumatic drugs (DMARDs; ex: methotrexate, azathioprine, leflunomide, belimumab, and antimalarials such as PLAQUENIL® and hydroxychloroquine).

In another embodiment, the patient is in remission and the methods comprise assessing recurrence, such as disease flares. SLE progresses in a series of flares, or periods of acute illness, followed by remissions. Disease-modifying antirheumatic drugs (DMARDs) are used preventively to reduce the incidence of flares, the process of the disease, and lower the need for steroid use; when flares occur, they are treated with corticosteroids. In one embodiment, the methods of the invention can thus be used to, for example, monitor the efficacy of DMARDs in reducing flares. In an alternative embodiment, the methods can be used, for example, to monitor the efficacy of steroids in treating flares. The methods of the invention can thus be used to gauge disease activity, monitor and/or predict response to treatments, and monitor and/or predict the onset of flares in SLE patients.

In one embodiment, the methods are in combination with SLEDAI scores (as are known in the art), to improve accuracy in monitoring SLE activity and/or in differentiating between active and non-active disease in a subject. An exemplary SLEDAI calculator that can be used in these embodiments is shown below.

The methods may comprise determining a level of any other markers as desired for a given purpose, together with modifying the SLE risk score based on a contribution of the additional markers. In one embodiment, the level of the one or more additional markers may be adjusted by one or more transformation analyses Any of the methods described herein can be used in combination with differential diagnostic assays. For example, antibodies directed against anti-cyclic citrullinated peptide antibody (anti-CCP antibodies) are specific serological markers for the diagnosis of rheumatoid arthritis (RA). In addition, antibodies to rheumatoid factor isotypes (RF IgM, IgA and IgG) are commonly used for the differential diagnosis of rheumatic diseases. Thus, any of the methods of the invention may further comprise contacting the sample with anti-CCP antibodies and/or IgM, IgG and IgA rheumatoid factors under conditions suitable to promote specific binding of the antibodies to their target antigen, removing unbound antibodies, detecting binding complexes between the antibodies and their targets in the sample, and comparing a level of such binding complexes to a standard, wherein an increase in such binding complexes relative to the standard indicates that the subject has RA. This embodiment helps serve to distinguish SLE from RA in the subject.

In a second aspect, the present invention provides methods for diagnosing systemic lupus erythematosus (SLE) comprising: (a) determining a level of double stranded DNA antibodies (anti-dsDNA), EC4d, and BC4d markers in a sample from a subject; (b) calculating an SLE risk score by adjusting the level of one or more of the markers by one or more transformation analyses; (c) comparing the SLE risk score to a standard; and (d) one or more of: (I) diagnosing the subject as having SLE based on the comparison; (II) determining a level of SLE disease activity based on the comparison; (III) providing the comparison to an entity for diagnosis of SLE; and (IV) providing the comparison to an entity for monitoring SLE disease activity.

All embodiments and combination of embodiments disclosed in the first aspect of the invention can be used in this second embodiment. Similarly, all common terms in this second aspect have the same meaning and embodiments disclosed for the first embodiment of the invention. As disclosed in the examples that follow, the inventors demonstrate that the methods of the invention provide specificity and sensitivity of SLE diagnosis and disease monitoring compared to previous methods.

The methods may comprise determining a level of any other markers as desired for a given purpose, together with modifying the SLE risk score based on a contribution of the additional markers. In one embodiment, the level of the one or more additional markers may be adjusted by one or more transformation analyses. Such additional markers include, but are not limited to, platelet C4d (PC4d) and erythrocyte CR1 (ECR1). The platelet fraction is can be from other blood components to allow analysis of platelet-bound complement activation products, such as PC4d. Platelet isolation can be performed with methods known in the art, including differential centrifugation or immunoprecipitation using antibodies specific for platelets (e.g., CD42b). The methods may further comprise determining a ratio of one or more of EC4d and ECR1; BC4d and ECR1; PC4d and ECR1. EC4D, PC4d, and BC4D tend to be elevated in SLE patients while ECR1 tends to be decreased. These ratios can be used in combination with the methods of the invention to help predict the likelihood of SLE. In one embodiment, the determination of the level of CR1 can be made using flow cytometric methods, with measurements taken by direct or indirect immunofluorescence using polyclonal or monoclonal antibodies specific for each of the molecules.

In one embodiment, the methods comprise a two tiered analysis. Embodiments of a two tiered analysis are provided in the examples that follow. The method comprises a first tier of determining the level of anti-dsDNA marker in a biological sample from the subject. If the level of anti-dsDNA marker is within a predetermined level, then the subject is diagnosed with SLE. However, if the level of anti-dsDNA marker is outside the predetermined level, then a second tier analysis comprises determining the level of EC4d, and BC4d markers in the sample. The subject is diagnosed with SLE if the level of the EC4d, and BC4d markers is within a predetermined level.

In another embodiment Tier 1 analysis involves both DS-DNA analysis and the signal intensity of cell-based complement activation product (CB-CAP) markers, EC4D and BC4D (and optionally PC4d). See, for example, FIG. 2. If the patient is positive on dsDNA testing or if the patient has an "extreme threshold" for the intensity of EC4D, PCD4, or BC4D (i.e. has a complement-bound cellular signal that is in the range of at least 6 standard deviations above the mean of that marker among non-lupus patients), then the patient is classified as positive for SLE. Patients that are negative on Tier 1 testing (i.e. negative for DS-DNA, which represents approximately 40-50% of all confirmed SLE patients, and have no extreme threshold results in the CB-CAPS analysis) are then evaluated in Tier 2. The Tier 2 analysis comprises determining a ratio of EC4D/ECR1 and/or BC4D/ECR1 to determine the SLE risk score. EC4D and BC4D tend to be elevated in SLE patients while ECR1 tends to be decreased. These ratios can be used to predict the likelihood of SLE or SLE disease activity.

In another embodiment, the methods comprise a three tiered analysis (See Example 1). Embodiments of a three tiered analysis are provided in the examples that follow. The method comprises determining the level of anti-dsDNA marker in a biological sample from the subject. If the level of anti-dsDNA marker is within a predetermined level, then the subject is diagnosed with SLE. However, if the level of anti-dsDNA marker is outside the predetermined level, then the level of EC4d and BC4d markers (and optionally platelet C4d (PC4d)) is determined in the sample. The Tier 2 analysis comprises determining whether the level or one, two, or all three of the EC4d, BC4d, and PC4d markers exceed an "extreme threshold" (i.e.: in the range of at least 6 standard deviations above the normal range for that marker). Subjects who have any of the EC4d, BC4d, and PC4d markers at or above the extreme level are declared suspect SLE patients at the specificity and diagnostic predictive accuracy established for Tier 2.

For the patient that does not exceed any of the extreme thresholds for the tested markers, the method then goes to a Tier 3 analysis, which comprises determining a ratio of EC4D/ECR1 and/or BC4D/ECR1 to determine the SLE risk score. EC4D and BC4D tend to be elevated in lupus patients while ECR1 tends to be decreased. These ratios predict the likelihood of lupus. Patients exceeding the established threshold for ratios are designated as suspect lupus patients at the specificity and diagnostic predictive accuracy established for Tier 3.

The methods of all aspects of the invention as described herein can be carried out manually or may be used in conjunction with an automated system or computer. For instance, the methods can be performed using an automated system, in which a subject's blood sample is analyzed to make the determination or determinations of levels of particular biomarkers, and the comparison with the pre-determined level or pre-determined range is carried out automatically by software appropriate for that purpose. Computer software, or computer-readable media for use in the methods of this invention include: a computer readable medium comprising: (a) code for receiving data corresponding to a determination of complement component C4d deposited on surfaces of red blood cells, platelets, or lymphocytes (e.g., B cells), and for data corresponding to an amount of anti-MCV, ANA, and/or anti-dsDNA antibodies in the biological sample; (b) code for retrieving a pre-determined level for complement component C4d deposited on surfaces of such cells of individuals, and for retrieving a predetermined level of anti-MCV antibodies, ANA, and/or anti-dsDNA antibodies is such samples; and (c) code for comparing the data in (a) with the pre-determined level of (b) to make a determination whether an accurate SLE diagnosis can be made or whether additional measurements of other biomarkers are required. In some embodiments, the computer readable medium further comprises (d) code for receiving data corresponding to a determination of complement receptor CR1 deposited on surfaces of red blood cells; (e) code for retrieving a pre-determined level for complement receptor CR1 deposited on surfaces of red blood cells of individuals; and (f) code for comparing the data in (d) with the pre-determined levels of (e).

In certain embodiments of the invention, one or more pre-determined levels or pre-determined ranges of biomarker levels may be stored in a memory associated with a digital computer. After data corresponding to a determination of complement C4d, anti-MCV antibodies, ANA, anti-dsDNA antibodies, and/or complement receptor CR1 is obtained (e.g., from an appropriate analytical instrument), the digital computer can compare the measured biomarker data with one or more appropriate pre-determined levels or pre-determined ranges. After the comparisons take place, the digital computer can automatically calculate if the data is indicative of SLE diagnosis.

Accordingly, some embodiments of the invention may be embodied by computer code that is executed by a digital computer. The digital computer may be a micro, mini or large frame computer using any standard or specialized operating system such as a Windows based operating system. The code may be stored on any suitable computer readable media. Examples of computer readable media include magnetic, electronic, or optical disks, tapes, sticks, chips, etc. The code may also be written by those of ordinary skill in the art and in any suitable computer programming language including, C, C++, etc.

Thus, the invention further comprises non-transitory computer readable storage medium comprising a set of instructions for causing a device for measuring marker levels in a sample to carry out the method of any aspect or embodiment of the invention. In a further aspect, the present invention provides non-transitory computer readable storage media, for automatically carrying out the methods of the invention on a computer linked to a device for measuring levels of the recited markers in a sample, such as a blood sample. As used herein the term "computer readable medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system. Any suitable device for measuring marker levels can be used, including but not limited to flow cytometry devices and devices for carrying our ELISAs.

The present invention also provides kits and combinations of tests for diagnosing SLE. In one embodiment, the present invention includes a combination of tests useful for diagnosing SLE comprising at least three of (i.e. 3, 4, or all 5): a first test for the level of EC4d, a second test for the level of BC4d, a third test for the level of anti-MCV antibodies, a fourth test for the level of ANA, and a fifth test for the level of anti-dsDNA antibodies. In some embodiments, the combination further comprises at least one additional test for determining the level of PC4d and/or ECR1. The kits or tests for determining the level of particular biomarkers include the various reagents for performing the measurements according to the methods described herein. For instance, in one embodiment, the kits or tests include reagents for performing immunofluorescence assays for each of the biomarkers, such as a conjugate of a monoclonal antibody specific for complement component C4d with a fluorescent moiety, and in some embodiments, a conjugate of a monoclonal antibody specific for complement receptor CR1 with a different fluorescent moiety. In certain embodiments, the kits or tests can include reagents for detecting antinuclear or anti-dsDNA antibodies, such as secondary antibodies labeled with a fluorescent tag, chemiluminescent tag, radiolabel tag or the like. Additionally, the kits can comprise such other material as may be needed in carrying out assays of this type, for example, buffers, radiolabeled antibodies, colorimeter reagents, instructions for separating different cell fractions from whole blood, and instructions for diagnosing SLE based on particular pre-determined levels of the biomarkers.

In another embodiment, the kits or tests include reagents for performing other standard assays for each of the biomarkers, such as ELISA or radioimmunoassays. In such embodiments, the kits or tests comprise monoclonal antibodies specific for C4d and CR1 conjugated with appropriate labels such as radioactive iodine, avidin, biotin or enzymes such as peroxidase. The kits can additionally comprise buffers, substrates for antibody-conjugated enzymes, instructions for separating different cell fractions from whole blood, and instructions for diagnosing SLE based on particular pre-determined levels of the biomarkers.

It is understood that the examples and embodiments described herein are for illustrative purposes only and that various modifications or changes in light thereof will be suggested to persons skilled in the art and are to be included within the spirit and purview of this application and scope of the appended claims. All references, publications, patents, and patent applications cited herein are hereby incorporated by reference in their entireties for all purposes.

EXAMPLES

Example 1

A Cell-Based Complement Activation Products Method for Diagnosing and Monitoring SLE This Example outlines an embodiment of the methods of the invention to classify a patient as having a high probability of suffering from SLE (or not) based on two pieces of diagnostic information: (1) presence or absence of anti-double-strand DNA antibodies (DS-DNA) by a standard ELISA assay; and (2) flow cytometric determination of cell-bound complement activation product levels (e.g., CB-CAPS assay). A flow chart depicting the multi-step method is shown in FIG. 1.

This multi-step approach involves three "tiers" of analysis. Tier 1 analysis involves DS-DNA analysis alone. Given the high specificity of double-strand DNA, a positive on DS-DNA is used to tentatively declare a patient positive for Lupus. CB-CAPS data for that patient is also collected for information related to monitoring and severity. A Tier 1 positive patient is displayed as DS-DNA+, suspect Lupus, with CB-CAPS analysis indicating whether the complement pattern is also consistent with Lupus. A patient Tier 1 positive has a result displayed with a specificity and diagnostic predictive accuracy value established for Tier 1 positives.

In the event that a patient is negative on DS-DNA, which represents approximately 40-50% of all confirmed SLE patients, then CB-CAPS analysis is used to evaluate the patient in Tier 2. An "extreme threshold" approach was used to develop a series of signal intensity cut-offs using three cell-based complement activation product (CB-CAP) markers, EC4D, PC4D, and BC4D, that are used to further characterize the probability of a patient being a lupus patient. Tier 2 analysis determines if any of the individual levels of the three CB-CAP markers exceeds the "extreme threshold." The extreme threshold was developed empirically from normal (e.g., healthy subjects) and/or subjects with an autoimmune disease other than SLE, and is designed to recognize a patient who has a complement-bound cellular signal that is in the range of 6-7 standard deviations above the normal range for that marker. Patients who have any of the three cellular markers at the extreme level are declared suspect lupus patients at the specificity and diagnostic predictive accuracy established for Tier 2.

For the patient that does not exceed any of the extreme thresholds for the three markers, the embodiment then goes to a Tier 3 analysis. In Tier 3, a recursive partitioning approach was used to develop threshold ratios of the signal intensity for EC4D/ECR1 and BC4D/ECR1 to determine the probability that a patient has lupus. EC4D and BC4D tend to be elevated in lupus patients while ECR1 tends to be decreased. These ratios predict the likelihood of lupus. Patients exceeding the established threshold for ratios are designated as suspect lupus patients at the specificity and diagnostic predictive accuracy established for Tier 3.

By using this step-wise approach, we are able to assign a diagnostic accuracy value to the probability that a patient has lupus or not. The confidence level of a positive result is related to the level at which the diagnosis is made. At the first tier, the very high specificity of DS-DNA gives a high confidence that this is in fact a lupus patient. The method can also use elevated levels of cell-bound complement to further enhance the confidence of this designation. At each Tier of analysis, a positive and negative predictive value is provided in the final report. The overall value of this approach is to provide as much information as possible from diagnostic tests themselves, while maintaining as high a specificity as possible during the diagnostic analysis.

Example 2

Figure 2:
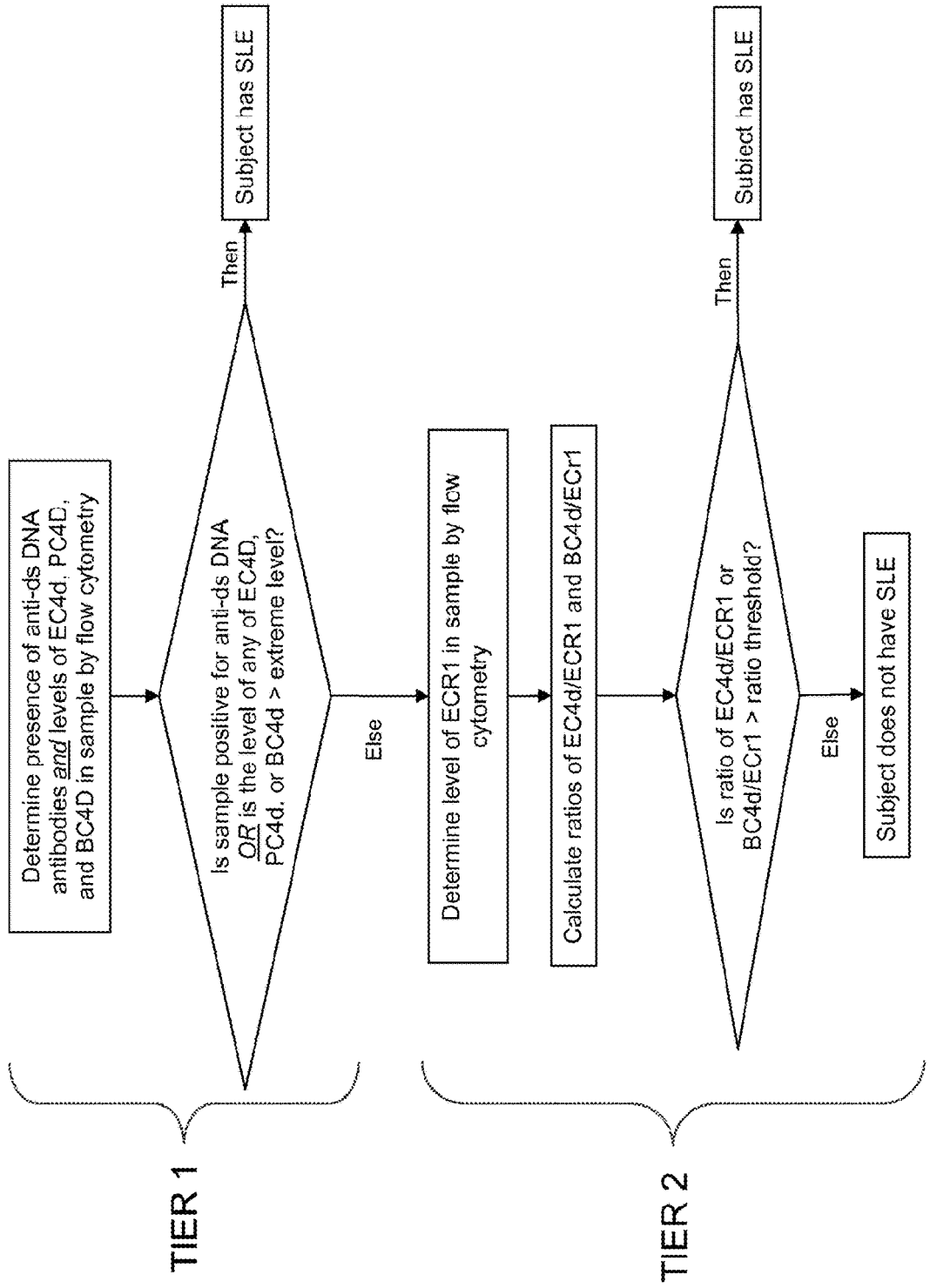
FIG. 2 is a flow chart illustrating an embodiment of the methods of the invention for diagnosing SLE based on blood sample levels of cell-based complement activation products containing two detection tiers.

A Cell-Based Complement Activation Products Method for Diagnosing and Monitoring SLE This Example outlines a second embodiment of the methods of the invention to classify a patient as having a high probability of suffering from SLE (or not), and provides a demonstration, based on two pieces of diagnostic information: (1) presence or absence of anti-double-strand DNA antibodies (DS-DNA) by a standard ELISA assay; and (2) flow cytometric determination of cell-bound complement activation product levels (e.g., CB-CAPS assay). A flow chart depicting the multi-step method is shown in FIG. 2.

This multi-step approach involves two "tiers" of analysis. Tier 1 analysis involves both DS-DNA analysis and the signal intensity of three cell-based complement activation product (CB-CAP) markers, EC4D, PC4D, and BC4D. If the patient is positive on dsDNA testing or if the patient has an "extreme value" for the intensity of EC4D, PCD4, or BC4D (i.e. has a complement-bound cellular signal that is in the range of 6-7 standard deviations above the mean of that marker among non-lupus patients), then the patient is classified as positive for lupus. A Tier 1 positive patient is displayed as either DS-DNA+, indicating a Lupus diagnosis, or with CB-CAPS results indicating a Lupus diagnosis, or both. A patient Tier 1 positive has a result displayed with a specificity and diagnostic predictive accuracy value established for Tier 1 positives.

Patients that are negative on Tier 1 testing (i.e. negative for DS-DNA, which represents approximately 40-50% of all confirmed SLE patients, and have no extreme value results in the CB-CAPS analysis) are then evaluated in Tier 2. In Tier 2, a recursive partitioning approach was used to develop threshold ratios of the signal intensity for EC4D/ECR1 and BC4D/ECR1 to determine the probability that a patient has lupus. EC4D and BC4D tend to be elevated in lupus patients while ECR1 tends to be decreased. These ratios predict the likelihood of lupus. Patients with ratios outside the bounds of established threshold ratios are designated as lupus patients at the sensitivity, specificity and diagnostic predictive accuracy established for Tier 1 and Tier 2 combined.

By using this step-wise approach, we are able to assign a diagnostic accuracy value to the probability that a patient has lupus or not. The confidence level of a positive result is related to the tier at which the diagnosis is made. At the first tier, the very high specificity of DS-DNA gives a high confidence that a DS-DNA positive patient is in fact a lupus patient. The elevated levels of any of the cell-bound complement further enhance the confidence of a Tier 1 positive patient designation as a lupus patient. At both Tiers of analysis, a positive and negative predictive value is provided in the final report. The overall value of this approach is to provide as much information as possible from the diagnostic tests themselves, while maintaining as high a specificity as possible during the diagnostic analysis.

We have applied the 2-Tiered embodiment to the group of patients summarized in Table 1 below.

TABLE 1

| Study Subjects | | |
|---|---|---|
| 589 Total Study Subjects | 208 SLE | 145 ds DNA− |
| | | 63 ds DNA+ |
| | 381 All Others | 202 Normal Healthy volunteers |
| | | 179 Other Rheumatic Diseases |

The SLE patients were diagnosed according to the ACR Criteria for the Classification of SLE. The Other Rheumatic Diseases included Rheumatoid arthritis (67%), systemic sclerosis (12%), dermatomyositis (5%), Sjogren's (5%), other vasculitis (4%), polymyositis (4%), and others (3%). All 589 study subjects were tested for dsDNA using a standard ELISA assay, and their levels of EC4D, BC4D, and PC4D were determined by flow cytometry, according to the Tier 1 strategy described above.

The results of Tier 1 are summarized in Table 2.

TABLE 2

| Tier 1 Test Results | | |
|---|---|---|
| Tier 1 Test* | Disease - Negative n (%) | Disease - Positive n (%) |
| Test + | 13 (3.41) | 103 (49.52) |
| Test − | 368 (96.59) | 105 (50.48) |
| Total | 381 | 208 |

*dsDNA Positive as defined by the manufacturer's instructions;
extreme value of EC4D in Other Rheumatic Disease + Normal Healthy group is 5.65 + 6 * 3.327 = 25.612;
extreme value for BC4D is 28.26 + 6 * 32.535 = 223.47;
extreme value for PC4D is 2.56 + 6 * 3.04 = 20.8

The Sensitivity for Tier 1 testing is 50%; the Specificity is 97%.

The Tier 1—negative study subjects were analyzed in Tier 2. The values for ECR1 were obtained by flow cytometry and the ratios of EC4D/ECR1 and BC4D/ECR1 were calculated. Recursive partitioning was used to establish the following rule for a positive test result:
(EC4D/ECR1>0.59 and BC4D/ECR1>3.69) OR (EC4D/ECR1<=0.59 and BC4D/ECR1>4.48)=>Test (+)

The results of Tier 2 testing are summarized in Table 3.

TABLE 3

| Tier 2 Test Results | | |
|---|---|---|
| Tier 2 Test* | Disease - Negative n (%) | Disease - Positive n (%) |
| Test + | 17 (4.62) | 46 (43.81) |
| Test − | 351 (95.38) | 59 (56.19) |
| Total | 368 | 105 |

Sensitivity: 44%;
Specificity: 95%

The results of the Tier 1 and Tier 2 analyses are summarized in Table 4.

TABLE 4

Summary of Two Tiered testing for Lupus diagnosis

| | | |
|---|---|---|
| Tier 1 | Sensitivity | 50% |
| (N = 589) | Specificity | 97% |
| Tier 2 (N = | Sensitivity | 44% |
| 473) | Specificity | 95% |
| Overall | Sensitivity | 72% |
| (N = 589) | Specificity | 92% |

Example 3

This example outlines a third embodiment of the methods of the invention wherein the likelihood of presenting with SLE as opposed to alternative rheumatic diseases is calculated based on an index derived from a multivariate logistic regression equation, in which the presence or absence of SLE is the classification variable and the serological markers together with CB-CAPS fragments deposited on circulating cells are independent variables, each of them associated with a coefficient.

In a study population of individuals comprising SLE patients, normal healthy volunteers (NHV) and patients with other rheumatic diseases, CB-CAPS (EC4D, PC4D, BC4d, ECR1), ANA and dsDNA antibodies were determined. The study was a multicenter, cross-sectional study that required one, or at most two, subject visits for screening and blood sample collection. There were no follow-up visits required. After the subject's informed consent was obtained, the following procedures were performed: The subject's medical history related to the diagnosis of any and all rheumatologic conditions was obtained and reviewed for inclusion/exclusion criteria and details regarding the diagnosis of these conditions were collected. The date of diagnosis was recorded for SLE and other rheumatologic conditions, and the specific SLE diagnostic criteria met was documented (revised ACR Criteria for the Classification of SLE); Subject demographics was documented (date of birth, gender, race/ethnicity). A urine pregnancy test via dipstick was performed on all females of child-bearing potential. Approximately 15 mL of patient's blood was obtained for analysis of CB-CAPS, dsDNA; the blood sample was obtained under either fasting or non-fasting conditions. The sample consisted of one 4.5 ml-EDTA tube (lavender top), and one 7.5 ml SST tube (red tiger top), which required centrifugation prior to shipping. All biological samples were sent by overnight delivery from the study site to the clinical laboratory (using transportation kits provided). Because CB-CAPS should be analyzed within 48 hours of sample collection, samples were not accepted on Saturday; therefore, subjects were only be enrolled from Monday through Thursday (Thursday shipping cut-off time is 10:00 a.m.). In order to preserve blinding in the analytical laboratory, case report forms and any subject information that would disclose the subject's diagnosis were faxed to the clinical project manager, whereas blood samples for analysis were sent directly to the analytical laboratory, accompanied by a completed subject-specific requisition form. Results of these tests were not made available to the investigator during the conduct of the study. Specimens were identified only by subject number and initials and the analytical lab remained blinded to subject-specific diagnosis. Only the clinical team had access to patients' diagnoses throughout the study. Erythrocytes, B-lymphocytes, and platelets were isolated, washed, immunofluorescently labeled using monoclonal and/or polyclonal antibodies specific for CR1 and the Cr-derived ligand C4d, and analyzed by flow cytometry using the assay validated in our clinical laboratory (see below section). Mean fluorescence intensity was used as an indicator of expression level of each cell surface marker; dsDNA were measured using an enzyme linked immunosorbent assay (ELISA, INOVA, San Diego Calif.).

Erythrocytes obtained from whole blood samples were tested using a panel of monoclonal antibodies to detect and measure cell surface levels of C4d and CR1 complement activation products. Sample aliquots of patient whole blood were diluted, washed, and stained with purified monoclonal antibodies against human C4d or CR1 (specific antibodies) and a non-specific antibody (MOPC-21 msIgG1k isotype control) for 45 minutes at 2-8° C. Samples were then washed and re-suspended in a solution containing goat anti-mouse antibody conjugated to fluorescein isothiocyanate (FITC) for 45 minutes at 2-8° C. (dark) to detect the cell surface bound monoclonal antibodies C4d or CR1. The cells were then washed and re-suspended in buffered saline for FACS analysis using a Beckman Coulter FC500 cytometer and CXP software. Light scatter (forward and side) gating parameters during acquisition were used to isolate the live erythrocytes for quantification of the non-specific and specific antibody binding (MFI) in the FL1 (FITC) channel. The MFI for the isotype background control (MOPC-21 msIgG1k) and each complement protein (C4d, CR1) from 20,000 events was obtained, and the net MFI was then determined by subtracting the non-specific MFI from the specific MFI results. B-lymphocyte cells obtained from patient whole blood samples were tested using the C4d monoclonal antibody to measure cell surface levels of C4d by FACS. Sample aliquots from whole blood samples were lysed using BD Pharm Lyse™ lysing solution (ammonium chloride-based lysing reagent) to remove red blood cells prior to staining with the monoclonal C4d antibody (45 minutes at 2-8° C.). Cell surface C4d staining was detected using the goat anti-mouse fluorescein isothiocyanate (FITC) antibody (45 minutes at 2-8° C., dark). A monoclonal antibody against human CD-19 (CD-19 reacts with the 95 kDa type I transmembrane glycoprotein expressed during all stages of B-cell differentiation and maturation) conjugated to R-phycoerythrin (R-PE) was used to detect the C4d complement activation derived fragment specific to the B-lymphocytes. Stained cells were washed and re-suspended in buffered saline for FACS analysis using a Beckman Coulter FC500 cytometer using CXP software to isolate the B-lymphocytes cells and to measure fluorescent staining intensity. Light scatter (forward and side) gating parameters were used during acquisition to isolate all lymphocytes (150,000 live events) followed by secondary gating based on positive CD-19 R-PE staining for analysis of the B-lymphocyte subset of cells. Quantification of the non-specific (MOPC-21 msIgG1 isotype control) and specific (C4d) fluorescence in the FL1 (FITC) channel was determined for the gated B-lymphocyte cell subset. As above, net MFI for each patient sample was determined by subtraction of the isotype control background MFI results from the specific C4d MFI results on gated B-lymphocyte cells only. Platelet cells obtained from patient whole blood samples were tested using the C4d monoclonal antibody to measure cell surface levels of C4d by FACS as above. Unwashed whole blood samples were diluted and stained with the monoclonal antibody against huC4d (45 minutes at 2-8° C.), followed by staining with goat anti-mouse conjugated to FITC (45 minutes at 2-8° C., dark). A monoclonal antibody against human CD-42b conjugated R-phycoerythrin (R-PE) to (platelet specific marker) was used to identify the C4d complement activation derived fragment specific to the platelets. FACS analysis was performed using a Beckman Coulter FC500 cytometer using CXP software to measure fluorescent staining intensity. Light scatter (forward and side) gating parameters were used during acquisition to isolate the platelet population followed by secondary gating based on positive CD-42b R-PE staining (platelets) for analysis of the platelet subset of cells. Quantification of the non-specific (MOPC-21 msIgG1 isotype control) and specific (C4d) fluorescence in the FL1 (FITC) channel was determined for the gated platelet cells (5000 events). s above, net MFI was determined by subtraction of the isotype control background MFI results from the specific C4d MFI results on gated platelet cells only.

The Inclusion Criteria in the clinical study were the following: Ability to read, understand, and sign the informed consent form; ≥18 years of age; Agreement to and able to have blood sample collected, subjects with rheumatologic conditions in the following two categories (Diagnosed with SLE according to the revised ACR Criteria for the Classification of SLE, Diagnosed with one of the following rheumatologic disorders: Anti-Phospholipid Syndrome; fibromyalgia (ANA+ patients only); systemic sclerosis; rheumatoid arthritis, polymyositis; dermatomyositis; Wegeners granulomatosus; polyarteritis nodosa; cryoglobulinemic vasculitis; leukocytoclastic vasculitis; other immunologic vasculitides; primary Sjogren's Syndrome). In addition normal adult healthy individuals were enrolled. The exclusion Criteria consisted of: for normal healthy volunteers only: Based on the Principal Investigator's judgment, clinically significant, concurrent morbidity including cardiovascular, psychiatric, neurologic, gastrointestinal (e.g., gastric or duodenal ulcers, inflammatory bowel disease, history of GI bleeds), metabolic, pulmonary (e.g., asthma, COPD), renal (including renal insufficiency), hepatic, hematologic, immunologic, endocrine (e.g., hypothyroidism, diabetes), active infection or history of chronic infectious disease (Hepatitis B or C or HIV), neoplastic disease, and/or history of weight loss surgery. Overt or laboratory evidence of primary immunodeficiency syndromes Pregnant or lactating women. Participating centers were encouraged to recruit an equivalent number of subjects with SLE and other rheumatologic conditions to ensure a balanced sample. Blood was drawn from each subject for CB-CAPS and dsDNA analyses. All data and blood samples submitted were kept strictly anonymous by the use of subject I.D. numbers. Each center was assigned a two digit site number, and each center assigned a secondary I.D. number. Each center was responsible for maintaining a list of study numbers and associated subject names at their site. All subject identifiers were removed from any supporting documentation and all blood samples were identified only by subject I.D. numbers and initials. In addition, the Sponsor's clinical laboratory was blinded to all subjects' diagnoses. The laboratory was responsible for data collection, data verification, and reporting of all data. All basic demographic data, medical history, and documentation of disease diagnostic criteria were collected on standard Case Report Forms (CRF). The logistic and sample treatment procedures were provided below: The laboratory provided a transportation kit for each enrolled subject, equipped with a coolant cartridge. Each transportation kit contained an EDTA (4.5 ml) tube, a red tiger SST tube (7.5 ml) and a transfer vial for collection of separated serum, if applicable (see below). A pre-printed airbill was also included in the transportation kit. Upon receipt of the transportation kit, the coolant cartridge was removed and placed in the freezer until needed for shipping. Upon enrollment of the subject and collection of blood in the EDTA and red tiger SST tubes, the following procedure were implemented: The SST sample was allowed to clot naturally and completely (approximately 10 minutes) at room temperature, then centrifuged as soon as possible thereafter to avoid hemolysis of the RBCs. Following the centrifugation, the serum was transferred to the serum collection vial provided, or it was left in the SST tube, depending upon the site's sample handling procedures. The EDTA blood tube, SST tube, and serum collection vial were all be placed immediately into the transportation kit with the coolant cartridge and shipped overnight the laboratory. Due to the time-sensitive nature of the CB-CAPS assay, blood samples were not collected or shipped after 10 a.m. on Thursdays. All samples will be shipped (San Diego facility) via overnight delivery. Patients' blood samples were prepared for pick-up and shipping as soon as possible after collection. In the event of a delay between collection and packaging for shipping, samples were refrigerated at 2-8° C. All subject records were identified only by initials and assigned subject I.D. numbers. Subjects' names were not to be transmitted to the laboratory. The study physician at each site kept a Master Subject List. Subjects, after having the study explained to them, gave voluntary and written informed consent and HIPAA authorization (in compliance with 21 CFR Parts 50 and 312) at the screening visit before participating in any study-related procedures. Each subject read, and signed an informed consent and an HIPAA authorization form after having an opportunity to discuss with the Study physician. All participating patients were aware that he/she may withdraw from the study at any time. The Informed Consent statement and HIPAA authorization contained all of the elements and mandatory statements as defined in the CFR. Signed copies of the informed consent and HIPAA authorization forms were given to the subject and both documents were placed in the study physician study files. A unique subject identification number was assigned at the time that the subject signs the informed consent form. CRFs were completed and faxed to the laboratory within 1 week of obtaining blood samples. The original CRFs were retained by the study site. All CRFs were completed in a neat, legible manner to ensure adequate interpretation of data. Black ink was used to ensure clarity of all reproduced CRFs. All references to specific subjects were made by use of initials and by assigned subject number, not by name. Subject confidentiality was maintained by deleting all names (marked through with black marker) in any reports or records submitted with the CRF. Any modification of previously entered data was made by striking through the original entry with a single line, initialing and dating the change, and entering the correct data. Use of opaque correction fluid, correction tape, and highlighters was prohibited. This study was conducted in compliance with the protocol and the ICH guidelines for Good Clinical Practice. No adverse event information was recorded for this study unless the event is related to the blood draw itself. Approval by the Institutional Review Board (IRB) prior to the start of the study was the responsibility of the study physician.

Statistical analysis was conducted using the R software with logistic regression analysis. Receiver operating curves were used as appropriate for each of the markers (univariate analysis) and also following the determination of an index value as the output of the multivariate logistic regression equation.

Results: A total number of 613 individuals were enrolled in the study from April to August 2010. A total of 15 sites participated. This consisted of 213 patients with a diagnosis of Lupus (90% females), 206 normal healthy volunteers (65% females) and 185 patients with other rheumatic diseases (80% females). Mean age in patients with SLE was 41±14 years (mean±SD), it was 41±13 years in normal healthy volunteers (mean±SD), and 57±13 in patients with other rheumatic diseases. A significant proportion of patients with other rheumatic diseases presented with a diagnosis of Rheumatoid arthritis.

TABLE 5

| Diagnosis | Number |
|---|---|
| Rheumatoid Arthritis | 125 |
| Systemic Fibrosis Limited | 13 |
| Dermatomyositis | 9 |
| Other vasculitis | 8 |
| Primary Sjogren's Syndrome | 8 |
| Systemic Fibrosis diffuse | 8 |
| Polymyositis | 7 |
| Fibromylagia (ANA+) | 2 |
| Wegener Granulomatosus | 2 |
| Antiphospholipid Syndrome | 1 |
| Systemic Fibrosis/Sjogren's | 1 |
| Polyarteris Nodosa | 1 |
| All other diseases | 185 |

Among the 613 individuals enrolled. 9 of them did not meet the inclusion criteria (4 protocol violation; 2 patients erroneously enrolled, 3 for other reasons). Thus 603 individuals were evaluable for the analysis. The Table below highlights the average levels of dsDNA, EC4d, PC4d, BC4d and ECR1 in normal healthy individuals compared to those with SLE and other diseases.

TABLE 6 dsDNA levels: Results are expressed as mean CI 95%.

| | DsDNA Means | Confidence −95% | Confidence +95% |
|---|---|---|---|
| Normal Healthy | 39 | 33 | 46 |
| Other diseases | 61 | 47 | 76 |
| SLE | 229 | 196 | 263 |
| All individuals | 113 | 99 | 128 |

TABLE 7

EC4D levels (Net MFI): Results are expressed as mean CI 95%

| | EC4D Means | Confidence −95% | Confidence +95% |
|---|---|---|---|
| Normal Healthy | 5.3 | 4.6 | 6.1 |
| Other diseases | 6.4 | 5.8 | 7.0 |
| SLE | 17.4 | 15.0 | 19.8 |
| All individuals | 9.9 | 8.9 | 10.9 |

TABLE 8

ECR1 levels (Net MFI): Results are expressed as mean CI 95%

| | ECR1 Means | Confidence −95% | Confidence +95% |
|---|---|---|---|
| Normal Healthy | 20.7 | 19.6 | 21.7 |
| Other diseases | 15.9 | 14.9 | 16.9 |
| SLE | 13.3 | 12.4 | 14.1 |
| All individuals | 16.6 | 16.0 | 17.2 |

TABLE 9

BC4d levels (Net MFI Results are expressed as mean CI 95%

| | BC4D Means | Confidence −95% | Confidence +95% |
|---|---|---|---|
| Normal Healthy | 23.5 | 21.4 | 25.7 |
| Other diseases | 34.2 | 26.8 | 41.6 |
| SLE | 96.9 | 82.6 | 111.3 |
| All individuals | 50.6 | 44.7 | 56.4 |

TABLE 10

PC4d levels (Net MFI Results are expressed as mean CI 95%

| | PC4D Means | Confidence −95% | Confidence +95% |
|---|---|---|---|
| Normal Healthy | 2.0 | 1.2 | 2.8 |
| Other diseases | 3.6 | 3.0 | 4.2 |
| SLE | 16.2 | 12.0 | 20.4 |
| All individuals | 7.5 | 5.9 | 9.1 |

Figure 4A:
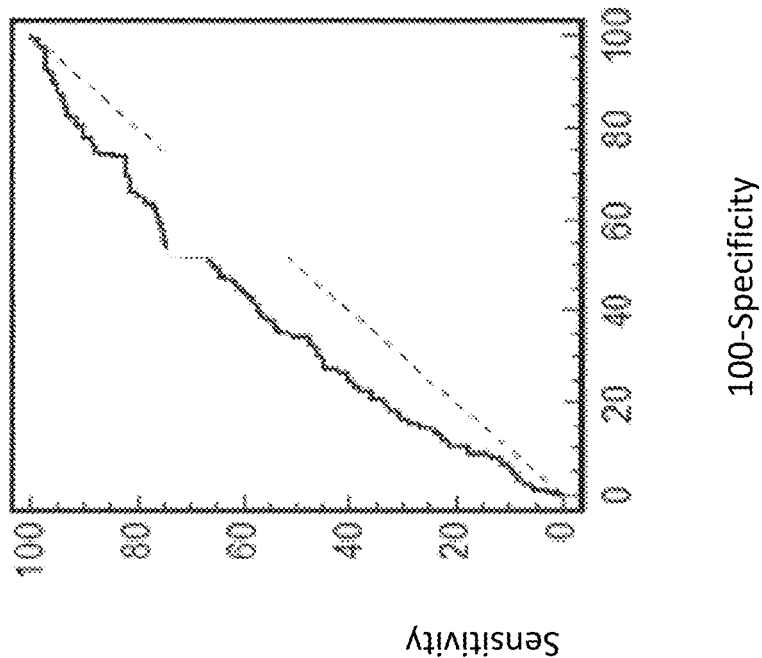
FIGS. 4A-4B are graphs demonstrating discriminating power of the ECR1 marker.
Figure 4B:
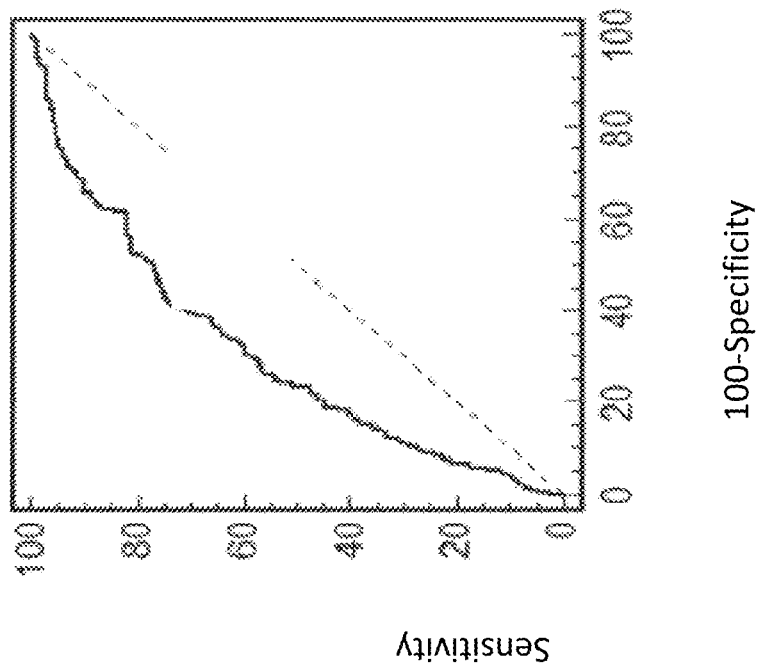
Figure 5A:
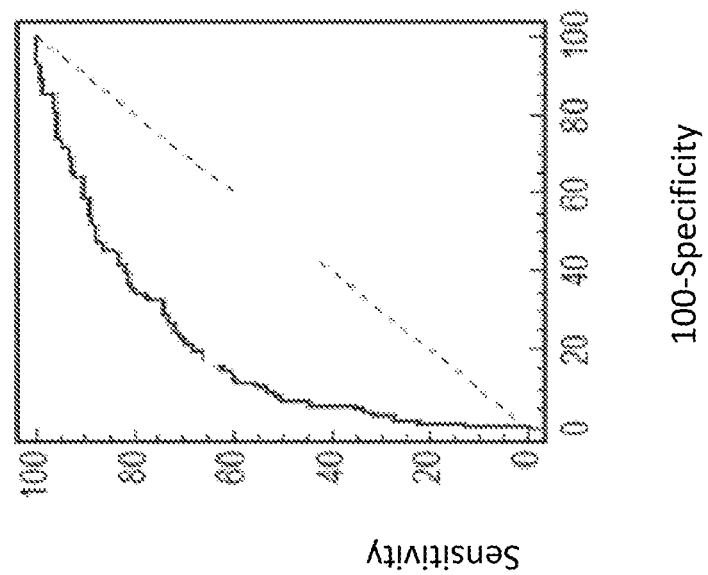
FIGS. 5A-5B are graphs demonstrating discriminating power of the BC4D marker.
Figure 5B:
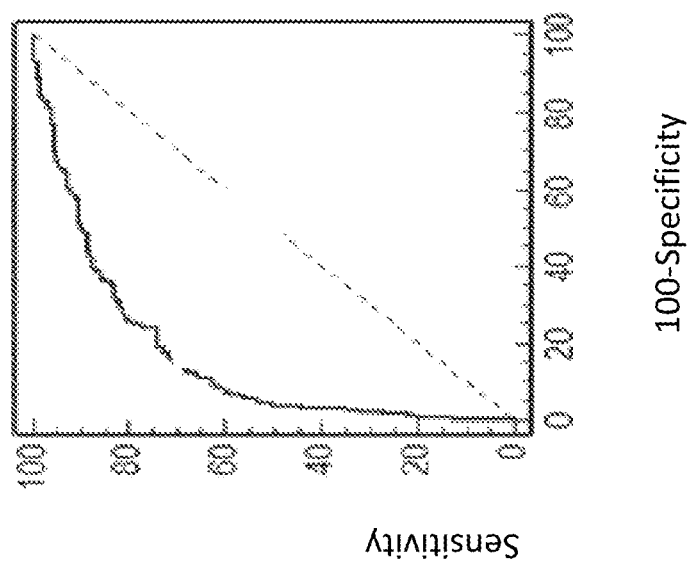

As a first step we tested the discriminating power for each of the biomarker (EC4D, ECR1, BC4d, PC4D) measured in the study. Results are presented in FIGS. 3-5 for EC4d, ECR1 and BC4d respectively. Clinical sensitivity and specificity for each of the marker including PC4D (using a preset cutoff at 20 Net MFI to account for the stability of the analyte during transportation) are given in the Table below and highlights the performance of each individual marker by univariate analysis.

TABLE 11

| | SLE vs All Others: Sens/Spec | SLE vs Other diseases Sens/Spec |
|---|---|---|
| EC4D (Net MFI) | 78%/80% | 69%/83% |
| ECR1 (Net MFI) | 74%/59 | 74%/48% |
| BC4D (Net MFI) | 71%/85% | 66%/83% |
| PC4D (>20U) (Net MFI) | 18%/99% | 18%/99% |

In 595 individuals comprising 209 patients with SLE, 205 normal healthy volunteers and 181 patients with other rheumatic diseases (121 of them with a diagnosis of rheumatoid arthritis), CB-CAPS and DsDNA antibodies were available for the multivariate logistic regression analysis. The study population was randomly divided (using R function) in a training set comprising a total of 219 individuals (54 NHV, 101 SLE, and 64 patients with other rheumatic diseases) to develop a model differentiating SLE patients from NHV and other diseases. The model developed in the training set was subsequently validated in an independent validation set of 384 individuals (112 SLE patients, 151 NHV and 121 other rheumatic diseases).

The multivariate linear logistic regression model was developed in the training set using the following initial predictors: positivity for DsDNA [cutoff at 301 unit as per manufacturer cutoff], EC4d (Net MFI), BC4d (Net MFI), ECR1 (Net MFI), PC4d (Net MFI). All Net MFI values were log normalized. An index reflecting the relative contribution of each biomarker in the logistic regression model was calculated. The validity of the index was subsequently tested in the validation set of individuals with SLE or other diseases (including NHV) as described above. Receiver operating curves (ROC) and area under the curves were determined and the index cutoff optimizing sensitivity and specificity was determined.

The multivariate logistic regression model from the training set revealed that DsDNA, EC4D and BC4d contributed significantly to the differential diagnosis of SLE versus other diseases and NHV. ECR1 and PC4d levels were not significantly contributing (data not shown). The following logistic regression equation was determined:

$$\text{Index} = -8.3919 + 1.4469*(\text{DsDNA} > 301) + 1.6194*\log(\text{EC4D}) + 1.4121*\log(\text{BC4D})$$

The Table below illustrates the coefficients, standard error and level of significance for each of the independent variable/analyte included in the model.

TABLE 12

|  | Estimate | Std. Error | P value |
|---|---|---|---|
| (Intercept) | −8.3919 | 1.1684 | 6.84e−13*** |
| DsDNA > 301TRUE | 1.4469 | 0.6915 | 0.0364* |
| log(EC4D) | 1.6194 | 0.3916 | 3.54e−05*** |
| log(BC4D) | 1.4121 | 0.3305 | 1.94e−05*** |

Figure 6:
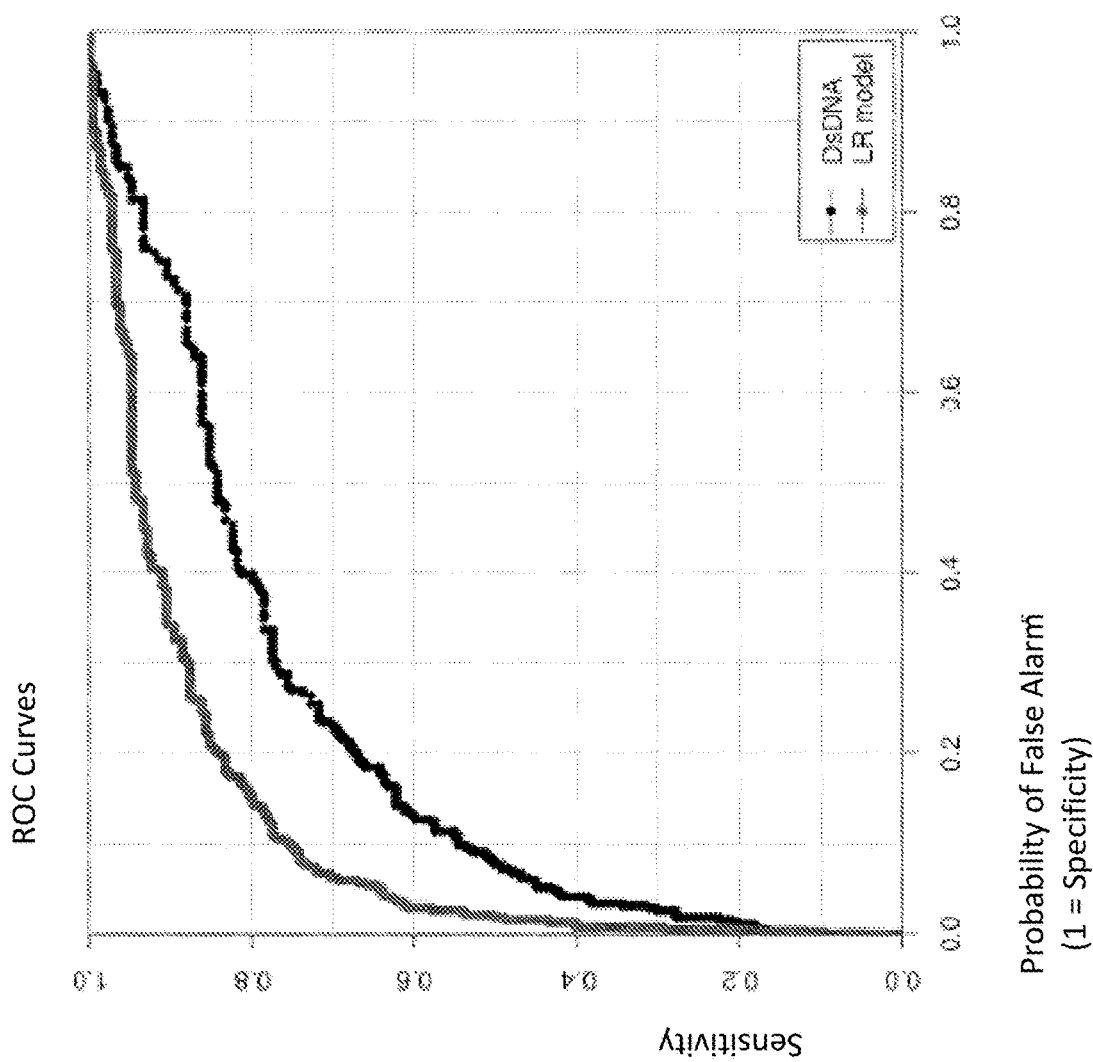
FIG. 6 is a graph showing ROC are under the curve for the index value calculated from the logistic regression equation using the combination of markers compared to that of dsDNA by univariate analysis.

As presented in the FIG. 6 there was significantly greater ROC AUC (and thus discriminating capabilities) for the index value calculated from the logistic regression equation described above (AUC=0.912) compared to that of dsDNA by univariate analysis (AUC=0.783). An optimal cutoff of 0 for the index value revealed the following clinical performances:

TABLE 13

| Index < 0 Indicates Positivity for SLE | SLE | NHV | Other diseases |
|---|---|---|---|
| Negative | 22 | 52 | 49 |
| Positive | 76 | 2 | 10 |

Sensitivity, specificity and accuracy are presented below and highlight the capability of the index to differentiate SLE patients from those with other diseases, or alternatively those NHV and with other diseases.

TABLE 14

|  | SLE vs NHV + Other diseases | SLE vs Other diseases |
|---|---|---|
| Accuracy % | 83.9 | 79.6 |
| Sensitivity % | 77.6 | 77.6 |
| Specificity % | 89.4 | 83.1 |

The logistic regression model developed in the training set (and associated optimal cutoff below or above 0) was subsequently tested independently in the validation set (384 individuals comprising 112 SLE patients, 151 NHV and 121 other rheumatic diseases).

As presented below the sensitivity, specificity and accuracy in the validation population were similar to those reported in the training set and illustrate the validity of the multivariate logistic regression model developed.

TABLE 15

| Index < 0 Indicates Positivity for SLE | SLE | NHV | RA | other Non-RA | Other disease |
|---|---|---|---|---|---|
| Negative | 20 | 139 | 37 | 50 | 87 |
| Positive | 91 | 12 | 24 | 9 | 33 |

TABLE 16

|  | SLE vs NHV + Other diseases | SLE vs Other diseases |
|---|---|---|
| Accuracy % | 83.0 | 77.1 |
| Sensitivity % | 82.0 | 82.0 |
| Specificity % | 83.4 | 72.5 |

Altogether, the following performances (cutoff at index=0) could be established by combining the individuals from the training and validation sets (n=595).

TABLE 17

|  | SLE | NHV | RA | other Non-RA | Other disease |
|---|---|---|---|---|---|
| Negative | 42 | 191 | 87 | 51 | 138 |
| Positive | 167 | 14 | 34 | 9 | 43 |

Clinical sensitivity, specificity and accuracy are described below and highlight the performances of the diagnostic method with a sensitivity, specificity and overall accuracy above 75%. ROC curve of the index value compared to dsDNA is presented in FIG. 4.

TABLE 18

|  | SLE vs NHV + Other diseases | SLE vs Other diseases |
|---|---|---|
| Accuracy % | 83.4 | 78.2 |
| Sensitivity % | 79.9 | 79.9 |
| Specificity % | 85.2 | 76.2 |

Figure 7:
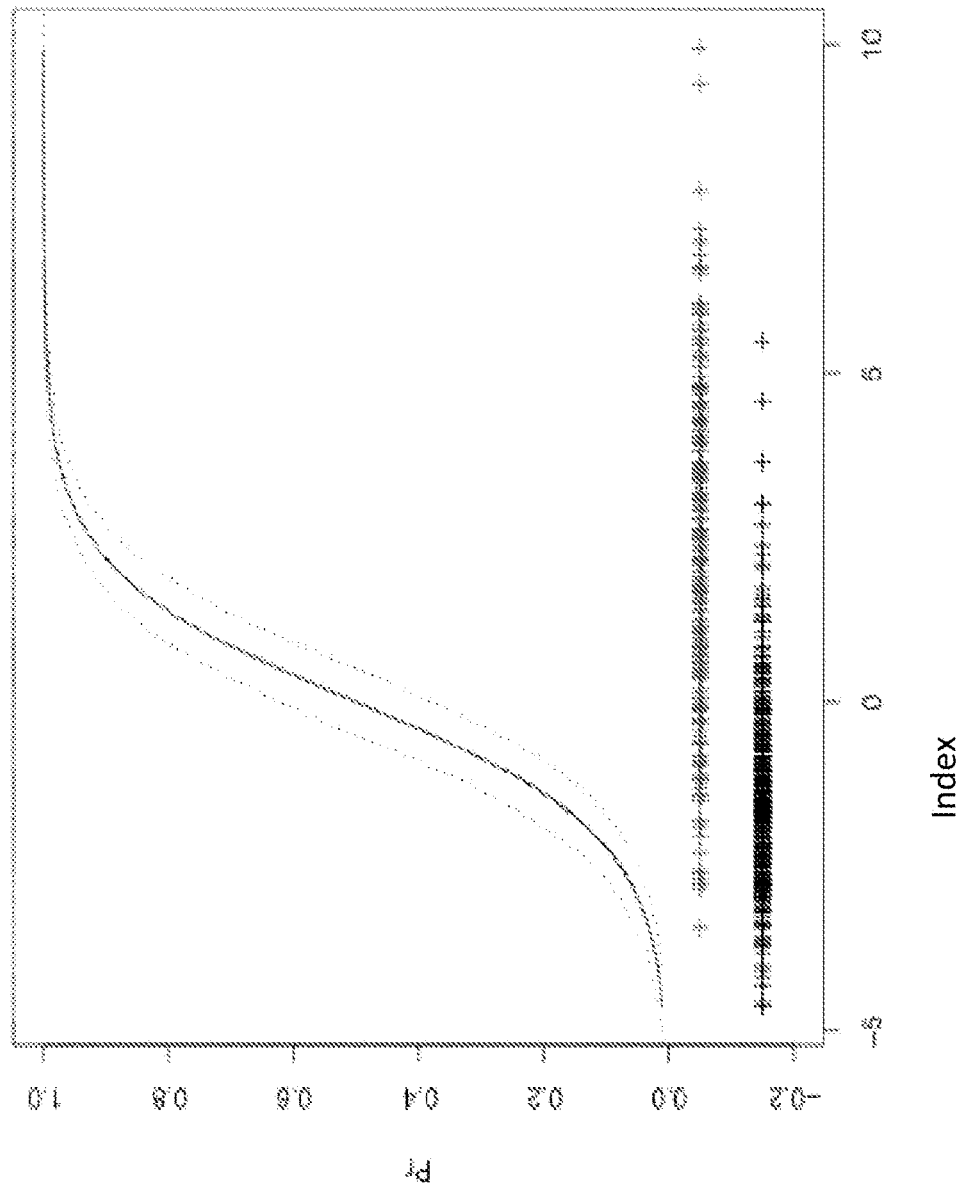
FIG. 7 illustrates the relationship between the index value and the probability to exhibit a diagnosis of SLE.

FIG. 7 illustrates the relationship between the index value and the probability to exhibit a diagnosis of SLE.

Example 4

This example outlines a fourth embodiment of the methods of the invention wherein the likelihood of presenting SLE as opposed to alternative rheumatic diseases is calculated based on an index derived from a multivariate logistic regression equation, in which the presence or absence of SLE is the classification variable and DsDNA and anti-MCV together with CB-CAPS fragments deposited on circulating cells are independent variables, each of them associated with a coefficient.

Anti-MCV levels were measured as per manufacturer instruction in 593 individuals enrolled in the study. Positivity for anti-MCV was observed in 43/210 patients with SLE (specificity of 79.5%), 5/205 normal healthy individuals (specificity of 95%), 79/119 patients with RA (sensitivity of 66%) and 8/59 patients with other diseases than rheumatoid arthritis (specificity of 86.4%). Multivariate logistic regression analysis revealed that anti-MCV positivity in combination with dsDNA, log EC4d and Log BC4d as indicated was contributing to the differential diagnosis of SLE versus other diseases.

Logistic regression coefficients in 388 patients were obtained (210 lupus patients and 178 patients with other diseases including 119 patients with rheumatoid arthritis).

TABLE 19

|  | Const.B0 | LOG_Ec4d | LOG_Bc4d | dsdna01 | MCV01 |
|---|---|---|---|---|---|
| Estimate | −6.199 | 1.467 | 1.013 | 1.258 | −1.796 |
| Standard Error | 0.780 | 0.263 | 0.217 | 0.474 | 0.317 |
| t(383) | −7.950 | 5.583 | 4.672 | 2.657 | −5.664 |
| p-level | 0.000 | 0.000 | 0.000 | 0.008 | 0.000 |
| −95% CL | −7.732 | 0.950 | 0.587 | 0.327 | −2.420 |
| +95% CL | −4.666 | 1.984 | 1.440 | 2.189 | −1.173 |
| Wald's Chi-square | 63.205 | 31.173 | 21.826 | 7.059 | 32.077 |
| p-level | 0.000 | 0.000 | 0.000 | 0.008 | 0.000 |
| Odds ratio (unit ch) | 0.002 | 4.336 | 2.754 | 3.519 | 0.166 |
| −95% CL | 0.000 | 2.587 | 1.798 | 1.387 | 0.089 |
| +95% CL | 0.009 | 7.269 | 4.219 | 8.927 | 0.310 |
| Odds ratio (range) |  | 1972.545 | 73.466 | 3.519 | 0.166 |
| −95% CL |  | 136.356 | 12.043 | 1.387 | 0.089 |
| +95% CL |  | 28535.170 | 448.176 | 8.927 | 0.310 |

Therefore, The logistic regression equation is as follow:
Index=−6.199+1.2581*(DsDNA>301)+1.4670*log(EC4D)+1.0132*log(BC4D)−1.7962*(antiMCV>20)

TABLE 20

| Diagnosis | INDEX Means | Confidence −95.000% | Confidence +95.000% | INDEX N |
|---|---|---|---|---|
| SLE | 1.94347 | 1.65717 | 2.229766 | 210 |
| Normal Healthy | −0.99169 | −1.13042 | −0.852954 | 205 |
| Other diseases | −1.18703 | −1.38776 | −0.986310 | 178 |
| All Grps | −0.01089 | −0.18327 | 0.161479 | 593 |

Figure 8:
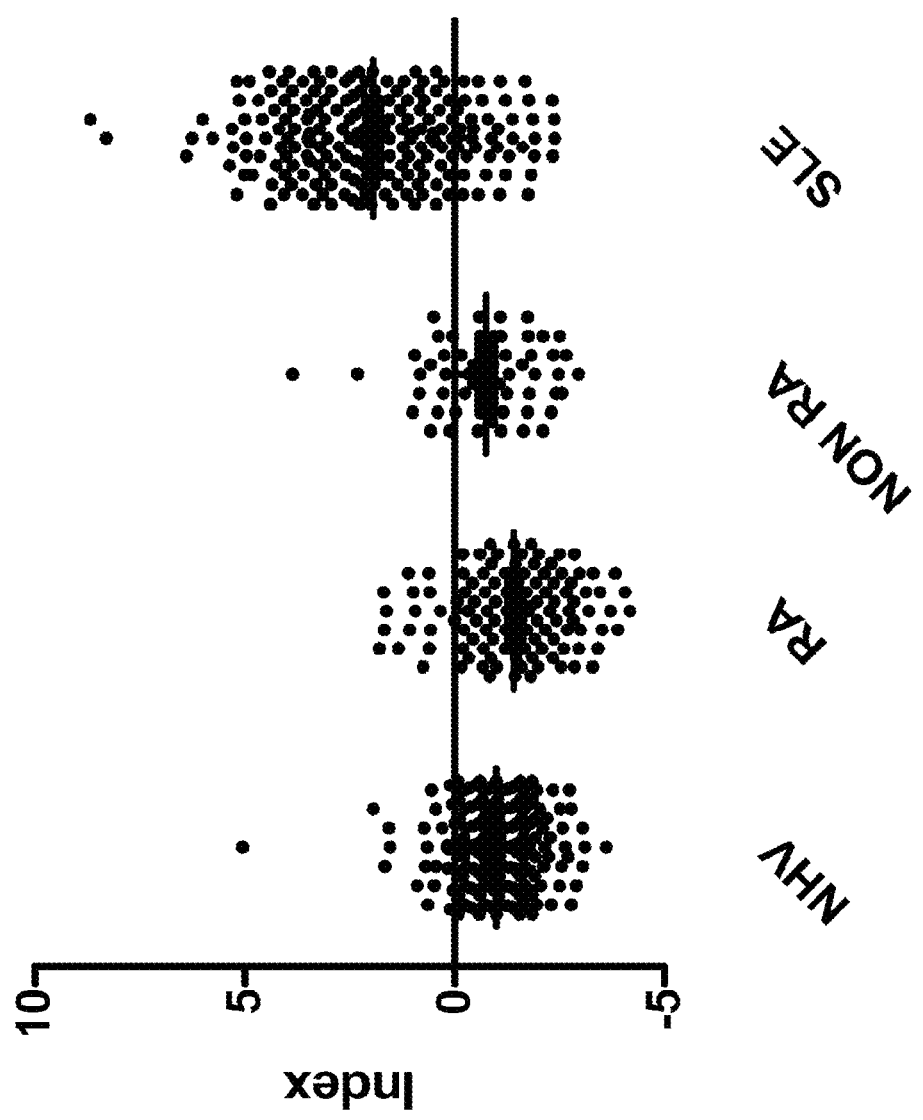
FIG. 8 is a graph demonstrating the distribution of index values by diagnostic.
Figure 9:
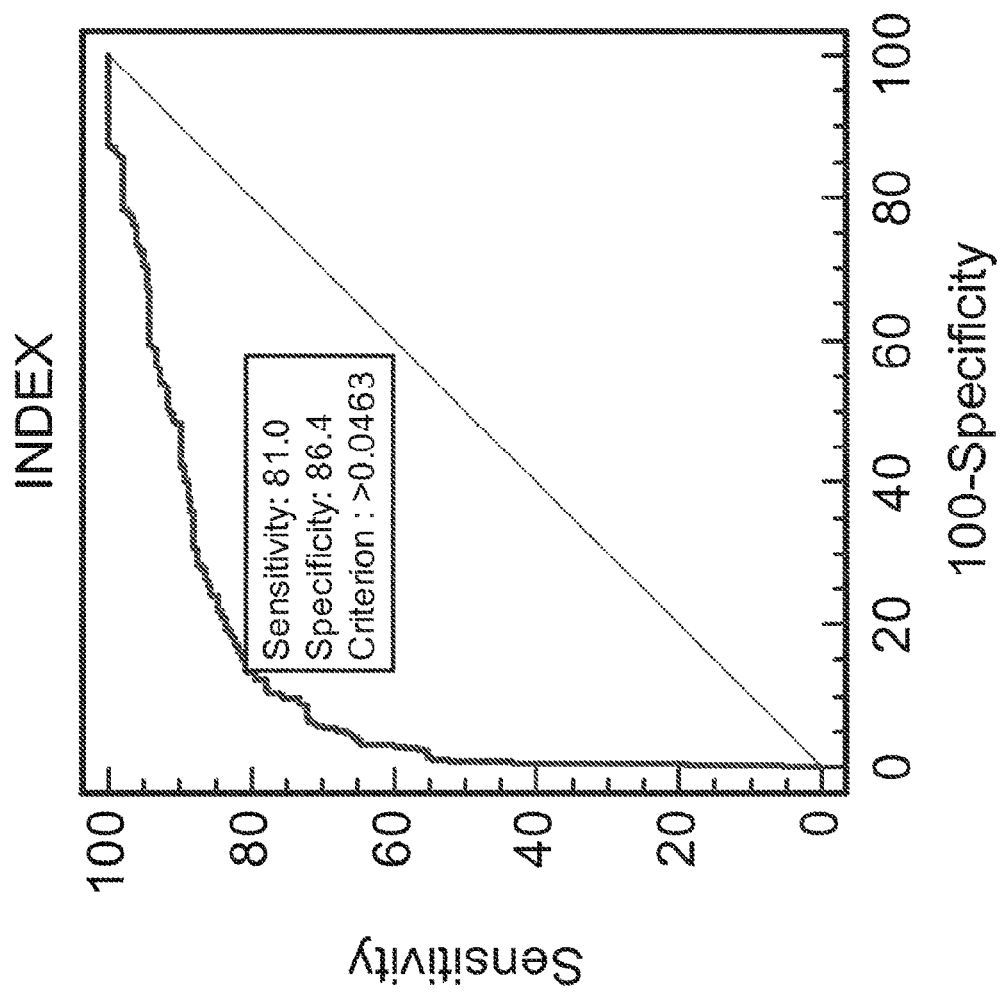
FIG. 9 is a graph illustrating the discriminative power of the index in the whole cohort.
Figure 10:
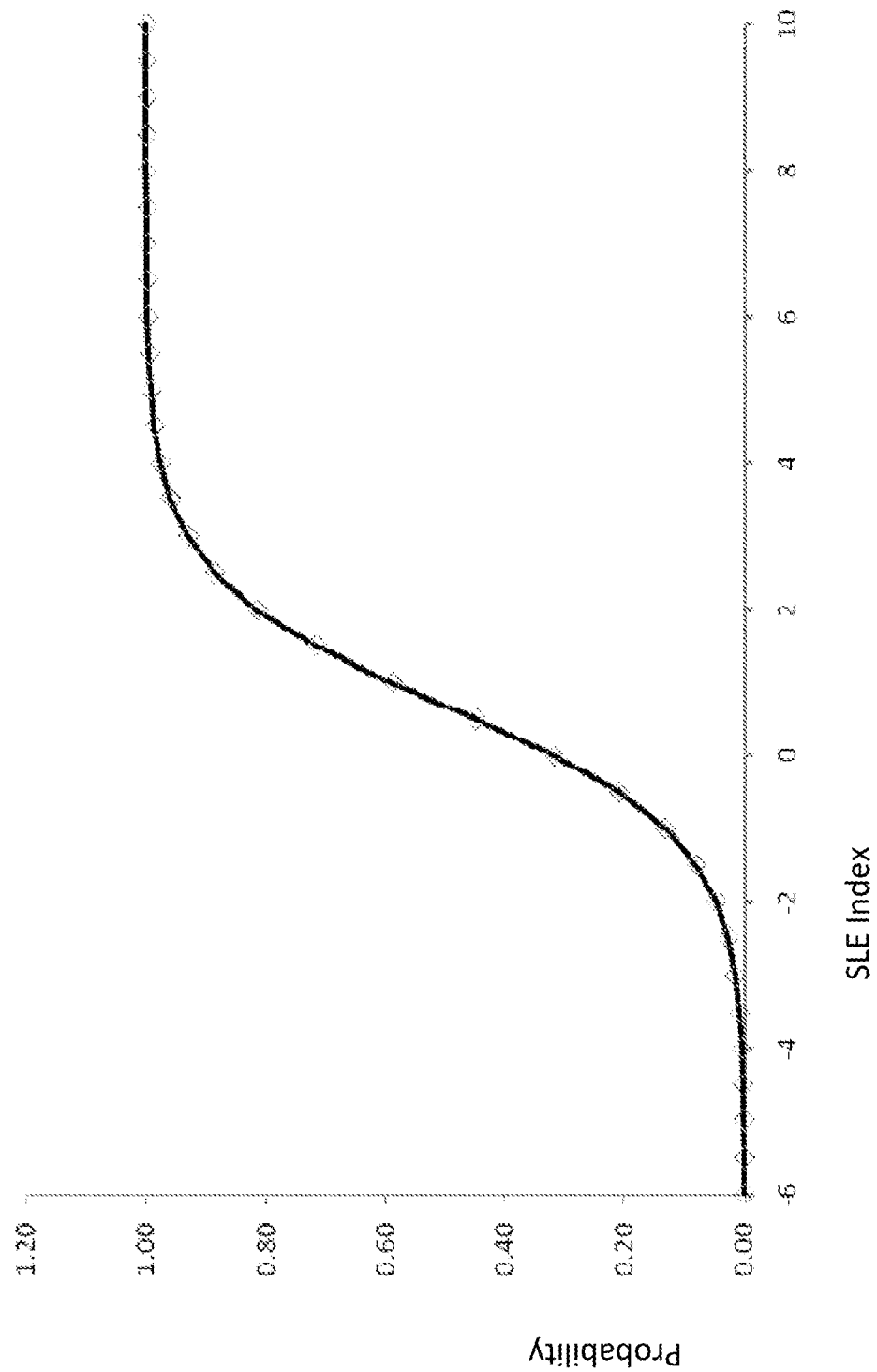
FIG. 10 is a graph illustrating the relationship between the index value and the probability to exhibit a diagnosis of SLE.

The distribution of index values by diagnostic is presented in FIG. 8. FIG. 9 illustrates the discriminative power of the index in the whole cohort. ROC curve AUC was 0.890. An index value above 0 was associated with a sensitivity of 81% (170 of 210) and a specificity of 86% in the whole cohort of patients. FIG. 10 illustrates the relationship between the index value and the probability to exhibit a diagnosis of SLE. Specificity against patients with other diseases is presented below:

TABLE 21

|  | All others | Normal Healthy individuals | Other diseases | Other disease non RA | Rheumatoid arthritis |
|---|---|---|---|---|---|
| Positive | 55 | 23 | 32 | 16 | 16 |
| Negative | 328 | 182 | 146 | 43 | 103 |
| specificity | 86% | 89% | 82% | 72% | 87% |

Altogether these data demonstrate that the addition of anti-MCV can provide significant improvement in the clinical performance of the index. However, the overall improvement in the specificity against RA patients was at the expense to the overall specificity against those with other diseases but without RA.

TABLE 22

| SLE vs Other diseases | Index: w/o antiMCV | Index: w antiMCV |
|---|---|---|
| Sensitivity | 79.9% | 80.9% |
| Specificity | 76.2% | 82.0% |
| Accuracy | 78.2% | 81.4% |

The difference in specificity of the index in the 59 other non RA diseases patients without (9 patients false positive) or with antiMCV (16 patients false positive) was 85% versus 72%. The difference was related to 5 additional patients misclassified in the presence of the index with anti-MCV (two patients with dermatomyositis, one patient with polymyositis, one patient with primary Sjogren's syndrome and one patient with diffuse systemic sclerosis).

The specificity for each of the other diseases enrolled in the study is presented in the following Table:

TABLE 23

|  | Index positive With antiMCV | number of patients | Specificity |
|---|---|---|---|
| APS | 1 | 1 | 0% |
| Vasculitis | 3 | 8 | 63% |
| Sjögren's Syndrome | 2 | 8 | 75% |
| Fibromyalgia (ANA+) | 0 | 2 | 100% |
| Sjögren's Syndrome + vasculititis | 0 | 1 | 100% |
| Systemic Sclerosis – Diffuse | 2 | 8 | 75% |
| Systemic Sclerosis – Limited | 3 | 13 | 77% |
| Rheumatoid Arthritis | 16 | 119 | 87% |
| Polymyositis | 2 | 7 | 71% |
| Dermatomyositis | 3 | 9 | 67% |
| Wegeners Granulomatosus | 0 | 2 | 100% |
| Grand Total | 32 | 178 | 82% |

The present method for the differential diagnosis of SLE can also integrate various serological markers associated the differential diagnosis of other rheumatic diseases. For example, the diagnosis of rheumatoid arthritis relies on the determination of rheumatoid factors (IgM, IgG, IgA). Therefore the determination of these serological markers described above will be integral to the discriminating power of the index we developed.

Example 5

This example outlines a fifth embodiment of the methods of the invention wherein the likelihood of presenting SLE as opposed to alternative rheumatic diseases is calculated based on an index derived from a multivariate logistic regression equation, in which the presence or absence of SLE is the classification variable and DsDNA, anti-MCV, and ANA together with CB-CAPS fragments deposited on circulating cells are independent variables, each of them associated with a coefficient.

ANA levels, DsDNA and AntiMCV levels were measured as per manufacturer instruction in 593 individuals enrolled in the study. The percentage of patients positive for these markers is presented in the Table below.

TABLE 24

|  | ANA (% pos) >20 units* | DsDNA (% pos) >301 units* | Anti-MCV (% pos) >20 units* |
|---|---|---|---|
| Normal Healthy | 9.2% | 0.5% | 5.4% |
| Other diseases | 41.0% | 5.1% | 49.4% |
| SLE | 88.5% | 30.0% | 20.5% |

Logistic regression coefficients in 388 patients (210 lupus patients and 178 patients with other diseases including 120 patients with rheumatoid arthritis).

TABLE 25

|  | Estimate | Std. Error z value | p value |
|---|---|---|---|
| (Intercept) | −6.4477 | 1.1847 | 5.25e−08*** |
| DsDNA > 301 | 1.0884 | 0.5085 | 0.0323* |
| ANA > 20 | 2.2181 | 0.3008 | 1.65e−13*** |
| LOG_EC4D | 1.3072 | 0.2792 | 2.84e−06*** |
| LOG_BC4D | 0.9518 | 0.2309 | 3.75e−05*** |
| Anti-MCV > 20 | 0.3413 | −4.529 | 5.93e−06*** |
| LOG_ECR1 | −0.4866 | 0.275 | 0.0769 |
| LOG_PC4D | 0.1041 | 0.161 | 0.5181 |

The Table illustrates the incremental value of EC4D, BC4D and antiMCV to the differential diagnosis of SLE versus other diseases.

TABLE 26

| Model | AUC |
|---|---|
| (DsDNA > 301) | 0.625 |
| (DsDNA > 301) + (ANA > 20) | 0.784 |
| (DsDNA > 301) + (ANA > 20) + LOG(EC4D) | 0.868 |
| (DsDNA > 301) + (ANA > 20) + LOG(EC4D) + LOG(BC4D) | 0.886 |
| (DsDNA > 301) + (ANA > 20) + LOG(EC4D) + LOG(BC4D) + MCV > 20) | 0.910 |

Therefore, The logistic regression equation with the highest predictive value is as follow:

Index=−6.150+0.996*(DsDNA>301)+1.480*(ANA>20)+1.422*log(EC4D)+0.876*log(BC4D)−1.883*(antiMCV>20).

The performance of the models on blinded subjects was estimated by repeatedly designing models from a random subset of the data, applying to the 'blinded' remainder, and compiling results. This technique, akin to in-silico validation, produces better estimates of performance than those that compute performance from classification of subjects previously used to design the models. In our analysis, 5,000 random subsets of 290 subjects each were used to generate models. Subsequently each model was applied to the 98 blinded subjects. As measures of performance, sensitivity and specificity were computed. For the NHV subjects, this was not necessary, as none of these subjects were used to generate models.

The Table below illustrates the index value in those normal healthy volunteers, those with other diseases and those with SLE.

TABLE 27

|  | Average (CI95%) |
|---|---|
| NHV | −1.65 (−3.636; 0.338) |
| Other diseases | −1.49 (−4.60; 1.62) |
| SLE | 2.14 (−1.99; 6.27) |

The distribution of index values by diagnostic is presented in FIG. 10.

TABLE 28

|  | Model1 | Model2 | Model3 | Model4 | Model5 |
|---|---|---|---|---|---|
| Sensitivity | 31.1 | 89 | 79.5 | 79.5 | 83 |
| specificity (other diseases) | 92.7 | 57.9 | 72.3 | 77.5 | 80.3 |
| Specificity (NHV) | 99.5 | 90.2 | 95.6 | 97.6 | 95.1 |

Model1: (DsDNA > 301)
Model 2: (DsDNA > 301) + (ANA 22 20)
Model 3: (DsDNA > 301) + (ANA > 20) + LOG(EC4D)
Model 4: (DsDNA > 301) + (ANA > 20) + LOG(EC4D) + LOG(BC4D)
Model 5: (DsDNA > 301) + (ANA > 20) + LOG(EC4D) + LOG(BC4D) + (MCV > 20)

The index value is in other diseases is presented in the Table below:

TABLE 29

|  | N | Index value | St Dev |
|---|---|---|---|
| Rheumatoid arthritis | 120 | −1.88 | 1.44 |
| Systemic Sclerosis | 21 | −0.82 | 1.56 |
| Dermatomyositis | 9 | −0.23 | 1.11 |
| Sjogren | 8 | −0.19 | 1.05 |
| Vasculitis | 8 | −0.72 | 2.53 |
| Polymyositis | 7 | −0.38 | 1.27 |
| Fibromyalgia | 2 | −2.76 | 1.10 |
| Wegeners Granulomatosus | 2 | −2.23 | 0.50 |
| Sjogren + fibromyalgia | 1 | −0.58 |  |

Figures 11A, 11B, 11C:
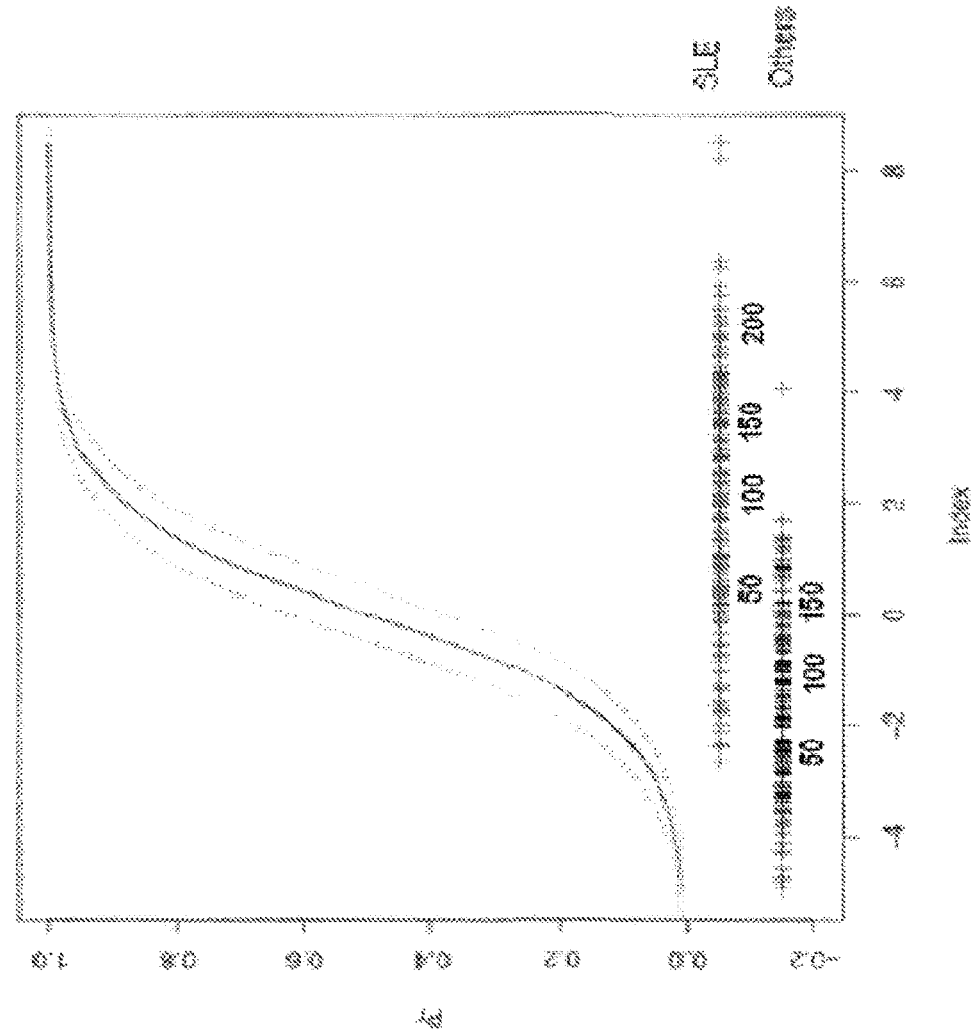
FIGS. 11A-11C are a summary (FIGS. 11A-11B) and graph (FIG. 11C) of probability to have SLE using the model integrating serological markers (ANA, DsDNA and anti-MCV) together with C4D levels deposited on erythrocytes and B cells.

FIGS. 11A-11C present the probability to have SLE using the present model integrating serological markers (ANA, DsDNA and anti-MCV) together with C4D levels deposited on erythrocytes and B cells. It also presents a method to report the results.

It is understood that the disclosed invention is not limited to the particular methodology, protocols and materials described as these may vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

Example 6

The study of CB-CAPS (EC4d, BC4d), ANA, dsDNA and anti-MCV in subjects with systemic lupus erythematosus versus Other Rheumatic Diseases and Healthy Normal Volunteers (referred to as "Capital") was initiated following the analytical validation EC4d and BC4d. The objective of this study was to establish the accuracy of the markers in discriminating between subjects with SLE and those with other similar diseases in the study population described above in Example 3.

Statistical analysis was conducted using the R software with logistic regression analysis. Receiver operating curves were used as appropriate for each of the markers (univariate analysis) and also following the determination of an index value as the output of the multivariate logistic regression equation.

A total of 210 SLE patients (90.5% females, mean age 42 y), 178 patients with other rheumatic diseases (80.3% females, mean age 57 y), and 205 healthy individuals (65.8% females, mean age 41 y) participated from April to August 2010. All patients gave informed consent. The group of patients with other rheumatic diseases consisted mainly of rheumatoid arthritis patients (n=120, 67%) and patients with systemic sclerosis (n=21, 12%).

TABLE 30

Characteristics of the 210 SLE patients

| | N (%) |
|---|---|
| Gender (females) | 190 (90%) |
| Race | |
| Caucasians | 75 (36%) |
| African Americans | 76 (36%) |
| Asians | 16 (8%) |
| Hispanics | 40 (19%) |
| Others | 3 (1%) |
| Malar rash | 91 (43%) |
| Discoid rash | 29 (14%) |
| Photosensitivity | 76 (36%) |
| Oral ulcers | 59 (28%) |
| Arthritis | 154 (53%) |
| Serositis | 59 (28%) |
| Pleuritis | 40 (19%) |
| Pericarditis | 26 (12%) |
| Renal disorder: | 86 (41%) |
| Proteinuria > 0.5 g/d | 80 (38%) |
| 3+ cellular casts | 9 (4%) |
| Neurologic disorder: | 15 (7%) |
| Seizures | 14 (7%) |
| psychosis without other causes | 2 (1%) |
| Hematologic disorder: | 113 (54%) |
| Hemolytic anemia | 8 (4%) |
| Leukopenia (<4000/L) | 59 (28%) |
| Lymphopenia (<1500/L) | 53 (25%) |
| Thrombocytopenia (<100,000/L) | 29 (14%) |
| Immunologic disorder: | 171 (81%) |
| anti-dsDNA | 140 (67%) |
| anti-Sm | 47 (22%) |
| anti-phospholipid | 57 (27%) |
| Antinuclear antibodies | 205 (98%) |

Univariate Analysis

Table 31 indicates the percentage positivity for serological markers together with EC4d, BC4d net mean fluorescence intensity (MFI) in each of the three groups.

TABLE 31

Percentage positivity for ANA, anti-dsDNA, anti-MCV, EC4d, and BC4d

| | SLE | Other diseases | Normal Healthy |
|---|---|---|---|
| ANA ≥ 20 units | 88.5% (186/210) | 41.0% (73/178) | 9.3% (19/205) |
| anti-dsDNA > 301 units (normal ≤ 301) | 29.5% (62/210) | 3.9% (7/178) | 0.5% (1/205) |
| Anti-MCV > 70 units (normal ≤ 70) | 1.9% (4/210) | 36.0% (64/178) | 0.5% (1/205) |
| EC4d Net MFI (CI 95%) | 17.6 (15.2-20.0) | 6.3 (5.7-6.8) | 5.3 (4.6-6.1) |
| BC4d Net MFI (CI 95%) | 110.4 (96.3-124.5) | 34.9 (26.1-41.6) | 23.5 (21.4-25.6) |

ROC curves with SLE and other diseases patients (total of 388 patients) revealed that an EC4d level above 8.9 units (Net MFI) resulted in a sensitivity of 70.0% and a specificity of 83% (AUC 0.825, CI95% 0.784 to 0.862) against other diseases patients. Alternatively, BC4d levels above 48 units (Net MFI) resulted in a sensitivity of 66% and a specificity of 86% (AUC 0.822, CI95% 0.780 to 0.858) against other diseases patients. Among the 205 normal healthy individuals, 15/205 of them presented with an EC4d level above 8.9 units (93% specificity) while 9 others exhibited BC4d levels above 48 units (96% specificity).

Multivariate Index Assay—Post Analytical Reduction of the Data

Anti-dsDNA was an insensitive (29.5%) yet highly specific (96%) marker for SLE. The multi-step approach involved two "tiers" of analysis. Tier 1 analysis involves DsDNA analysis alone in which positivity for dsDNA (>301 units) was associated with a diagnosis of lupus. In the second tier analysis corresponding to 523 anti-anti-dsDNA negative individuals, a multivariate logistic regression analysis revealed that SLE was associated with ANA positivity (ANA≥20 units, p<0.001), anti-MCV negativity (positivity for Anti-MCV>70 is affected with a negative coefficient, p<0.001), and elevation of both log normalized (LOG) EC4d and BC4d net MFI (p<0.001) (ROC area=0.907). A summary of the results are presented in Table 32.

TABLE 32

Summary of Results of Multivariate Index Assay

| | Estimate | Odd Ratio | P value |
|---|---|---|---|
| (Intercept) | −8.08 | | <2e−16 |
| ANA ≥ 20 Units | 2.2833 | 9.81 | 2.17e−14 |
| AntiMCV > 70 units | −2.6575 | 0.07 | 3.40e−05 |
| LOG(EC4d) | 1.1526 | 3.17 | 2.85e−05 |
| LOG(BC4d) | 1.1165 | 3.05 | 2.42e−06 |

An Index Equation corresponding to the output of the logistic regression model follows:

Equation 1 Index equation in dsDNA negative patients $$\text{Index} = -8.08 + 2.2833 \times \text{ANA20} - 2.6575 \times \text{AntiMCV70} + 1.1526 \times \log(\text{EC4d}) + 1.1165 \times \log(\text{BC4d})$$

ANA20: If ANA levels are above 20 units, the result is entered as 1; if ANA<20 Units the result is entered as 0; AntiMCV70: If anti-MCV levels are above 70 units, the result is entered as 1; if antiMCV≤70 Units the result is entered as 0. Log corresponds to the natural log of net MFI for EC4d and BC4d.

An example of index calculation form a patient enrolled in the CAPITAL study is provided below.

TABLE 33

SLE Patient 05-011. DsDNA negative patient (75 units, <301 units)

| Analyte | Results | Component index | Index Calculation | Interpretation |
|---|---|---|---|---|
| ANA | 133 Units | ANA20 = 1 | = −8.080 + 2.2833 × 1 − | Index > 0; |
| AntiMCV | <20 units | AntiMCV70 = 0 | 2.6575 × 0 + 1.1526 × 3.632 + | Consistent |
| ECd4 | 37 units | logEC4d = 3.632 | 1.1165 × 4.627 = | with SLE |
| BC4d | 102 units | logBC4d = 4.627 | 3.54 | |

Figure 12:
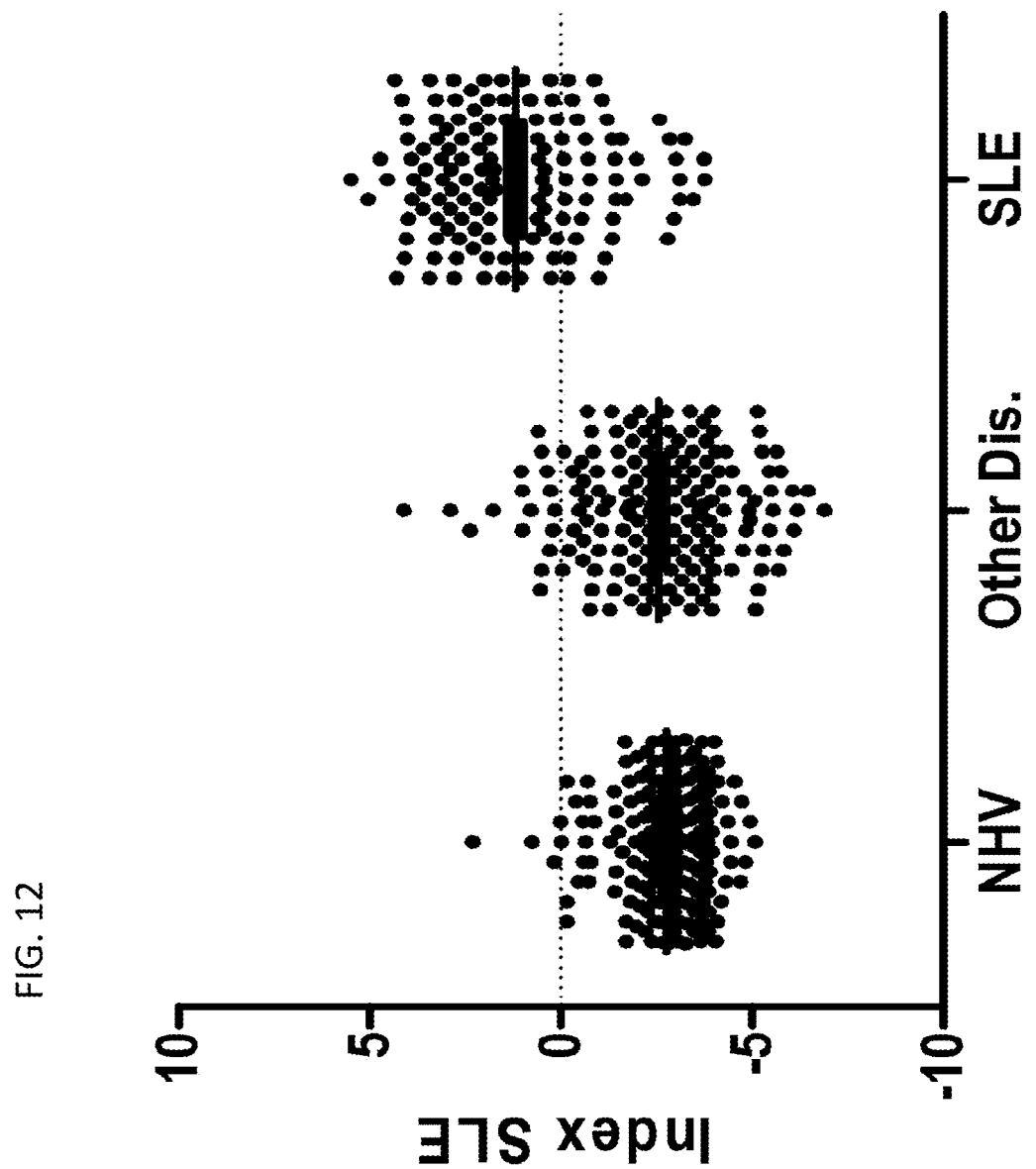
FIG. 12 is a graph demonstrating index value in dsDNA negative patients.

An Index score (see FIG. 12) corresponding to a weighted sum of these four markers was 1.20 (CI95%: 0.86; 1.53) in SLE, −2.53 (CI95%: −2.83; −2.24) in other rheumatic diseases, and −2.74 (CI95%: −2.89; −2.59) in normal healthy volunteers (NHV). Sensitivity was 71.6%, specificity against other diseases was 90.1% patients and 97.6% against normal healthy (Table 34).

Figure 13:
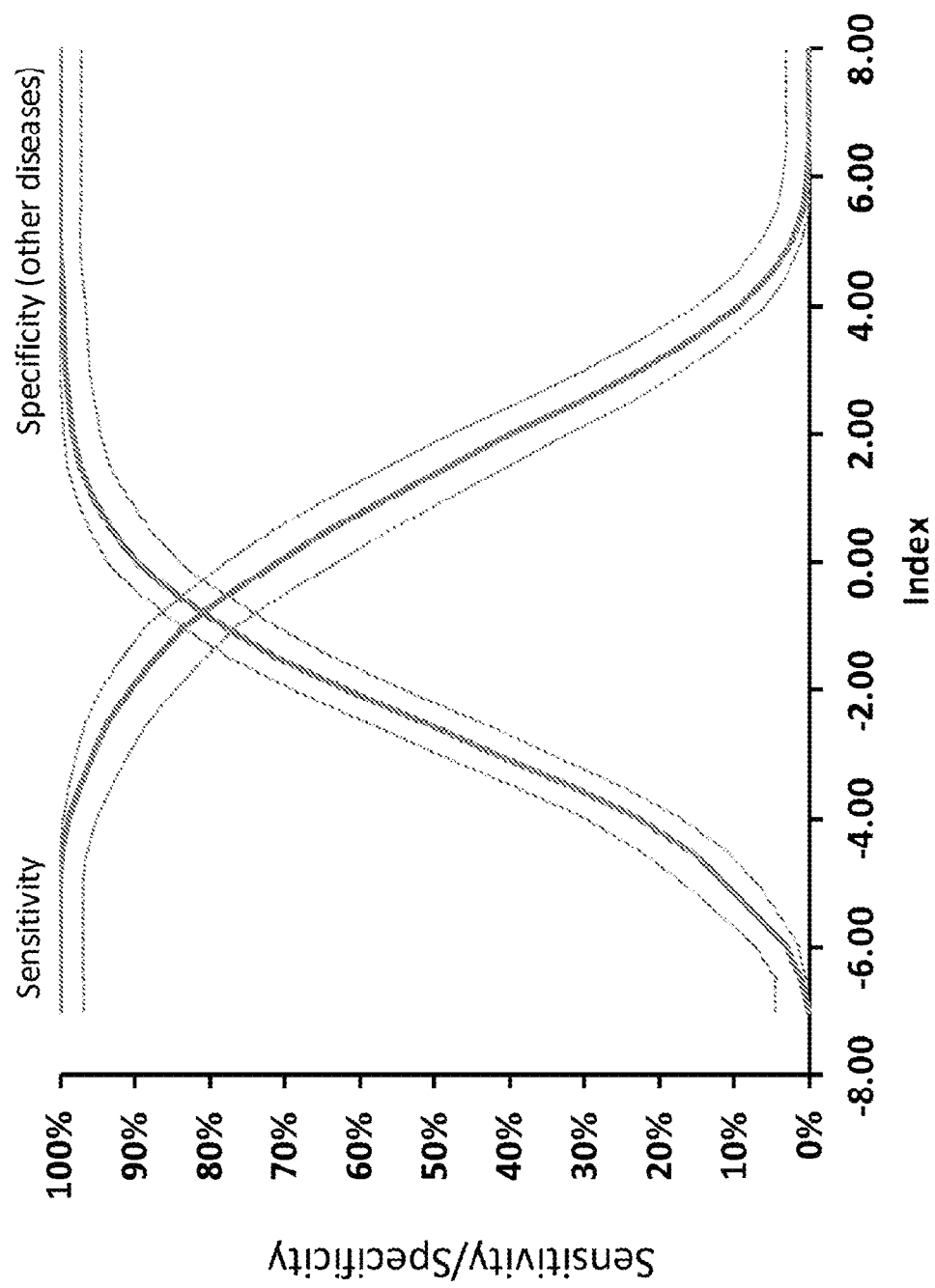
FIG. 13 is a graph demonstrating sensitivity and specificity as a function of the index.

A combination of anti-dsDNA positivity and the Index score (using a cutoff of zero) yielded 80.0% sensitivity for SLE, and 86.6% specificity in distinguishing SLE from other rheumatic diseases (97.1% specificity in distinguishing SLE from healthy subjects) (see Table 34). FIG. 13 illustrates the sensitivity and specificity (vs. other diseases) at any given index value.

TABLE 34

Clinical performances: Combination of Anti-dsDNA Positivity + Index Score

| | N | Nb positives | SLE | Other diseases | Normals |
|---|---|---|---|---|---|
| dsDNA (tier 1) | 593 | 70 | 62/210 (29.5%) | 7/178 (3.9%) | 1/205 (0.5%) |
| Index (tier 2) | 523 | 128 | 106/148 (71.6%) | 17/171 (9.9%) | 5/204 (2.4%) |
| TOTAL | 593 | 198 | 168/210 (80.0%) | 24/178 (13.4%) | 6/205 (2.9%) |

N = number

FIG. 14 illustrates the Tier analysis method. In Tier 1 positivity for dsDNA (levels>301 units) is associated with a diagnosis of SLE. Among dsDNA negative patients the index score composite of ANA (by ELISA, cutoff at 20 units), EC4d and BC4d levels measured by FACS (Net MFI) and anti-MCV (by ELISA, cutoff at 70 Units) is calculated. An Index above 0 is consistent with a diagnosis of SLE. While the index score is calculated using ANA determined by ELISA, Indirect immuno-fluorescence is performed when ANA is negative by ELISA. The specificity against patients with other rheumatic diseases is presented in Table 35 and ranged from 63% to 100%.

TABLE 35

Specificity against patients with other rheumatic diseases

| Diagnosis | N | Tier1 dsDNA positive | Tier2 Index > 0 | Total Positive | Specificity |
|---|---|---|---|---|---|
| Rheumatoid arthritis | 120 | 6 | 3 | 9 | 93% |
| Scleroderma | 21 | 1 | 4 | 5 | 76% |
| Dermatomyositis | 9 | 0 | 3 | 3 | 67% |
| Vasculitis | 8 | 0 | 3 | 3 | 63% |
| Sjogren's | 8 | 0 | 2 | 2 | 75% |
| Polymyositis | 7 | 0 | 2 | 2 | 71% |

TABLE 35-continued

Specificity against patients with other rheumatic diseases

| Diagnosis | N | Tier1 dsDNA positive | Tier2 Index > 0 | Total Positive | Specificity |
|---|---|---|---|---|---|
| Wegeners Granulomatosus | 2 | 0 | 0 | 0 | 100% |
| Fibromyalgia | 2 | 0 | 0 | 0 | 100% |
| Sjogren + fibromyalgia | 1 | 0 | 0 | 0 | 100% |

N = number

Moreover, as presented in Table 36 the addition of EC4d, BC4d and anti-MCV increased the AUC from 0.808 (dsDNA+ANA) to 0.918 (dsDNA+ANA+EC4d+BC4d+antiMCV).

TABLE 36

Performances characteristics

| | dsDNA + ANA | dsDNA + ANA + EC4d | dsDNA + ANA + EC4d + BC4d | dsDNA + ANA + EC4d + BC4d + antiMCV |
|---|---|---|---|---|
| SLE Positive | 187 | 159 | 163 | 168 |
| SLE Negative | 23 | 51 | 47 | 42 |
| Normal healthy positive | 20 | 6 | 3 | 5 |
| Normal healthy negative | 185 | 199 | 202 | 200 |
| Other diseases positive | 74 | 41 | 31 | 24 |
| Other diseases negative | 104 | 137 | 147 | 154 |
| Sensitivity (%) | 89 | 75.7 | 77.6 | 80 |
| Specificity, Other diseases (%) | 58.4 | 77 | 82.6 | 86.5 |
| Specificity Normal healthy (%) | 90.2 | 97.1 | 98.5 | 97.6 |
| AUC | 0.808 | 0.887 | 0.903 | 0.918 |

The day to day reproducibility of the Index were also determined in a total of 23 samples from 11 patients with SLE enrolled in the analytical validation study (erythrocytes and B lymphocyte C4d levels). None of these patients were part of the clinical validation study. The Index was determined 4 consecutive times on 4 consecutive days. The average standard deviation was 0.15 (range 0.04 to 0.31).

Equivocal Index Results Based on ANA and Anti-MCV Equivocal Values

Because the index cumulates two components (ANA and antiMCV) associated with a cutoff value, the index can potentially change from positive to negative (or vice versa) based on the analytical error at the medical decision limit for ANA (20 units) or anti-MCV (70 units). For example, in Table 37 the index can changes from −0.28 (case 1, ANA negative) to +2.00 (case 2, ANA positive) based on two unit difference in ANA at the decision limit (19 vs 21 Units)

TABLE 37

Effect of ANA cutoff on Index

| | ANA Units | AntiMCV Units | EC4d Net MFI | BC4d Net MFI | ANA20 | Anti MCV70 | INDEX | PATTERN |
|---|---|---|---|---|---|---|---|---|
| Case1 | 19 | 10 | 10 | 100 | 0 | 0 | −0.28 | NON SLE |
| Case2 | 21 | 10 | 10 | 100 | 1 | 0 | 2.00 | SLE |

It follows that equivocal results for the Index are preferably be defined when ANA and/or anti-MCV levels are near the cutoff value (and therefore potentially able to affect the positivity or negativity of the index). We defined an equivocal ANA when ANA levels ranged from 16 to 24 Units (20% CV at the 20 Units cutoff) and an equivocal anti-MCV when anti-MCV levels ranged from 56 to 84 units (20% CV at the 70 Units cutoff).

Figure 15:
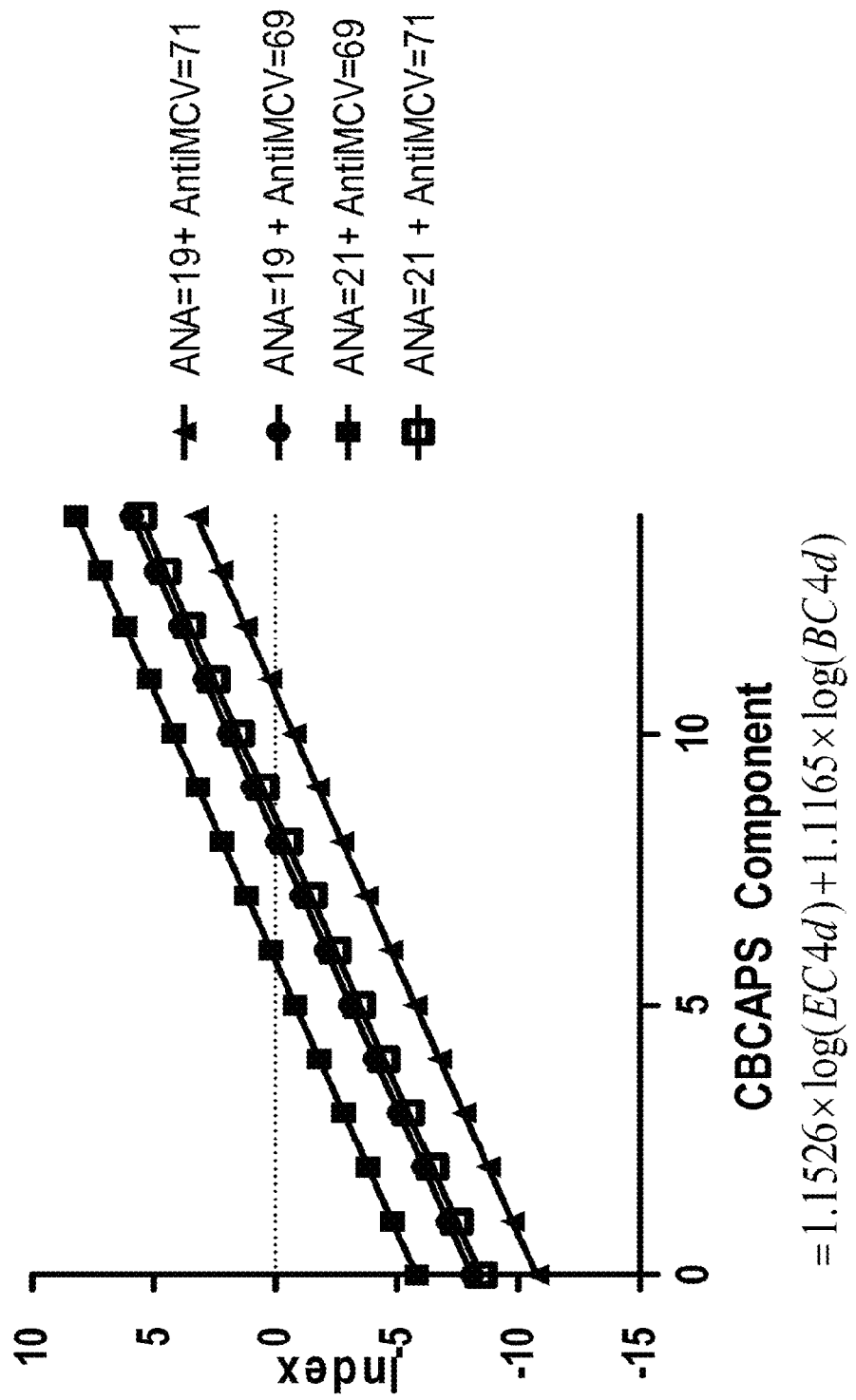
FIG. 15 is a graph demonstrating the effect of the CB-CAPS component on the index when ANA and Anti-MCV are equivocals.

As presented in the FIG. 15 the change in the index value from positive to negative is also heavily dependent on the CBCAPS component in the multi-index assay equation. A decision rule based on equivocal results for ANA and anti-MCV was established (Table 38). In the CAPITAL study a total of 15/523 patients dsDNA negative patients presented with an equivocal result (2.8%: 3 SLE, 3 other diseases and 7 normals). When these patients were excluded from the analysis the sensitivity was 72.0% (103/143), specificity against other diseases was 90.5% patients (152/168) and 98.4% (194/197) against normal healthy analysis (see Tier 2 analysis in Table 34 for comparison). While on a population basis these sensitivity and specificity values are similar, the results will be reported as equivocal on a per patient basis.

Equivocal Zone Based on Analytical Error at the Index of Zero

The accuracy at the medical decision limit (index of 0), and the definition of an equivocal zone was established at the 95% confidence interval based on 1.96 time the average standard deviation observed in the validation samples reported above (0.15). This corresponds to an equivocal zone of −0.3 to 0.3.

Table 39 indicates the performances characteristics of the index (Tier 2, dsDNA negative patients) in all patients compared to the performances without equivocal. As expected higher performance characteristics were achieved without equivocal results.

TABLE 39

Performances characteristics of the tier 2 analysis with equivocals

| Tier 2 dsDNA negative | N | Sensitivity SLE | Specificity Other diseases | Specificity Normals |
|---|---|---|---|---|
| All | 523 (100%) | 106/148 (71.6%) | 154/171 (90.0%) | 199/204 (97.5%) |
| Without equivocals based on ANA and anti-MCV cutoffs | 508 (97.1%) | 103/143 (72.0%) | 152/168 (90.4%) | 194/197 (98.5%) |
| Without equivocals based on ANA and anti-MCV cutoffs + error at Index = 0 | 482 (92.2%) | 99/130 (76.1%) | 148/160 (92.5%) | 6/205 (99.0%) |

A total of 8.8% patients presented either an equivocal result based on the uncertainty at the medical decision limit for ANA and antiMCV. As presented in the patient report enclosed, the performance characteristics reported are those calculated from the whole population (inclusive of equivocal index results based on equivocal ANA and Anti-MCV) A cautionary note is added on the patient report and stipulates

TABLE 38

Definition of Equivocal Results

| | 16 < ANA units | 16 ≤ ANA ≤ 24 units | ANA > 24 units |
|---|---|---|---|
| AntiMCV < 56 units | NOT EQUIVOCAL | Equivocal if CBCAPS component between 5.80 and 8.08 | NOT EQUIVOCAL |
| 56 ≤ AntiMCV ≤ 84 | Equivocal if CBCAPS component between 8.08 and 10.74 | Equivocal if CBCAPS component between 5.80 and 10.74 | Equivocal if CBCAPS component between 5.80 and 8.45 |
| AntiMCV > 84 | NOT EQUIVOCAL | Equivocal if CBCAPS component between 8.45 and 10.74 | NOT EQUIVOCAL | that the results should be interpreted with caution if the Index value is comprised between −0.3 and 0.3.

Validation Study

The Diagnostic method was validated prospectively in an independent cohort of patients with SLE and other rheumatic diseases. The study was in collaboration with the Lupus Center of Excellence (Pittsburgh, PA under Susan Manzi, MD and Joseph Ahearn, MD). None of the patients enrolled at the center were part of the patients enrolled in the CAPITAL study.

After the subject's informed consent was obtained blood was obtained for analysis of CB-CAPS, dsDNA, and ANA; The sample consisted of one 10 ml-EDTA tube (lavender top), and one 5 ml SST tube (goldtop), which required centrifugation prior to shipping. All biological samples were sent by overnight delivery from the Lupus Center of Excellence site to Exagen Diagnostics (using transportation kits provided). Because CB-CAPS should be analyzed within 48 hours of sample collection, samples were not accepted on Saturday; therefore, subjects were only enrolled from Monday through Thursday. In order to preserve blinding in the analytical laboratory, CRFs and any subject information that would disclose the subject's diagnosis were not provided to the laboratory. Specimens were identified only by subject number and initials and the analytical lab remained blinded to subject-specific diagnosis. Erythrocytes and B-lymphocytes were isolated, washed, immunofluorescently labeled using monoclonal and/or polyclonal antibodies specific for Cr-derived ligand C4d, and analyzed by flow cytometry using the assay validated in our clinical laboratory (see above section). Mean fluorescence intensity was used as an indicator of expression level of each cell surface marker; dsDNA, ANA and antiMCV were measured using an enzyme linked immunosorbent assay (ELISA).

Results

From Jun. 8, 2011 to Sep. 30, 2011 a total of 52 patients were enrolled in the validation study. This consisted of 36 patients with SLE, and 16 patients with other rheumatic diseases (among them 7 patients presented with rheumatoid arthritis, and 5 patients had Primary Sjogren's syndrome). Table 40 highlights the performances of the serological markers and CB-CAPS.

TABLE 40

Comparison between SLE Patients with Other Rheumatic Diseases

|  | SLE | Other diseases |
|---|---|---|
| ANA ≥ 20 units | 72% (26/36) | 50% (8/16) |
| anti-dsDNA > 301 units (normal ≤ 301) | 22% (8/36) | 6% (1/16) |
| Anti-MCV > 70 units (normal ≤ 70) | 3% (1/36) | 18% (3/16) |
| EC4d Net MFI (CI 95%) | 14.0 (9.5-18.5) | 5.2 (3.9-6.6) |
| BC4d Net MFI (CI 95%) | 53.4 (35.4-71.4) | 21.3 (14.8-27.8) |
| EC4d > 8.9 Units | 50% (18/36) | 6% (1/16) |
| BC4d > 48 Units | 36% (13/36) | 6% (1/16) |

Anti-dsDNA was an insensitive (22%, 8 positives) yet highly specific (94%) marker for SLE. The multi-step approach involving the two "tiers" as developed above was applied. The index score in dsDNA negative patients was −0.22 (CI 95%: −1.28; 0.84) in SLE (28 patients) and −2.63 (CI95%: −3.86; −1.41) in other rheumatic diseases (15 patients). The combination of anti-dsDNA positivity and the Index score (using a cutoff of zero) yielded 67% sensitivity for SLE, and 88.0% specificity in distinguishing SLE from other rheumatic diseases (see Table 41). This sensitivity was not significantly different from the sensitivity observed in the CAPITAL study (81%; p=0.117). Similarly, specificities between the two studies were identical (86.5% vs. 87.5%; p=1).

TABLE 41

Specificity in distinguishing SLE from other rheumatic diseases

|  | N | Nb positives | SLE | Other diseases |
|---|---|---|---|---|
| dsDNA (tier 1) | 52 | 9 | 8/36 (22.2%) | 1/16 (6.3%) |
| Index (tier 2) | 43 | 17 | 16/28 (57.1%) | 1/15 (6.3%) |
| TOTAL | 52 | 26 | 24/36 (66.7%) | 2/16 (12.5%) |

Note
one patient (number 111522) with SLE presented an equivocal result.
ANA was 23 Units and the Index value was −2.23 Units (non SLE).

Note one patient (number 111522) with SLE presented an equivocal result. ANA was 23 Units and the Index value was −2.23 Units (non SLE).

As presented in Table 42 the addition of EC4d, BC4d and anti-MCV increased the AUC from 0.588 (dsDNA+ANA) to 0.762 (dsDNA+ANA+EC4d+BC4d+antiMCV).

TABLE 42

Performances Characteristics

|  | dsDNA + ANA | dsDNA + ANA + EC4d | dsDNA + ANA + EC4d + BC4d | dsDNA + ANA + EC4d + BC4d + antiMCV |
|---|---|---|---|---|
| SLE Positive | 26 | 24 | 23 | 24 |
| SLE Negative | 10 | 12 | 13 | 12 |
| Other diseases positive | 8 | 4 | 1 | 2 |
| Other diseases negative | 8 | 12 | 15 | 14 |
| Sensitivity (%) | 72.2 | 66.7 | 63.9 | 66.6 |
| Specificity (%) | 50.0 | 75.0 | 93.8 | 87.5 |
| AUC | 0.588 | 0.679 | 0.731 | 0.762 |

Overall Clinical Performances

Altogether, the following performance characteristics can be derived when the CAPITAL study is combined with the validation study:

TABLE 43

|  | SLE | Other diseases |
|---|---|---|
| ANA ≥ 20 units | 87% (213/246) | 41% (81/194) |
| anti-dsDNA > 301 units (normal ≤ 301) | 28% (70/246) | 4% (8/194) |
| Anti-MCV > 70 units (normal ≤ 70) | 2% (4/246) | 34% (67/194) |
| EC4d > 8.9 Units | 67% (165/246) | 16% (32/194) |
| BC4d > 48 Units | 61% (151/246) | 13% (25/194) |

The combination of anti-dsDNA positivity and the Index score (using a cutoff of zero) yielded 78% sensitivity for SLE, and 86.6% specificity in distinguishing SLE from other rheumatic diseases (97.1% specificity in distinguishing SLE from healthy subjects) (Table 44).

TABLE 44

Combination of anti-dsDNA positivity and Index score (using a cutoff of 0)

|  | N | Nb positives | SLE | Other diseases | Normals |
|---|---|---|---|---|---|
| dsDNA (tier 1) | 645 | 79 | 70/246 (28.45) | 8/194 (4.1) | 1/205 (0.5%) |
| Index (tier 2) | 566 | 145 | 122/176 (69.3%) | 18/186 (9.6%) | 5/204 (2.4%) |
| TOTAL | 645 | 224 | 192/246 (78.0) | 26/194 (13.4%) | 6/205 (2.9%) |

As presented in Table 45 the addition of EC4d, BC4d and anti-MCV increased the AUC from 0.787 (dsDNA+ANA) to 0.893 (dsDNA+ANA+EC4d+BC4d+antiMCV).

TABLE 45

Performances Characteristics

|  | dsDNA + ANA | dsDNA + ANA + EC4d | dsDNA + ANA + EC4d + BC4d | dsDNA + ANA + EC4d + BC4d + antiMCV |
|---|---|---|---|---|
| SLE Positive | 213 | 183 | 186 | 192 |
| SLE Negative | 33 | 63 | 60 | 54 |
| Normal healthy positive | 20 | 6 | 3 | 5 |
| Normal healthy negative | 185 | 199 | 202 | 200 |
| Other diseases positive | 82 | 45 | 32 | 26 |
| Other diseases negative | 112 | 149 | 162 | 168 |
| Sensitivity (%) | 86.6 | 74.4 | 75.6 | 78.0 |
| Specificity Other diseases (%) | 57.7 | 76.8 | 83.5 | 86.6 |
| Specificig Normal healthy (%) | 90.2 | 97.1 | 98.5 | 97.6 |
| AUC | 0.787 | 0.859 | 0.875 | 0.893 |

The overall specificity in other rheumatic diseases (n=194) is presented in Table 46 and ranged from 56% to 100%.

TABLE 46

Specificity against patients with other rheumatic diseases

| Diagnosis | N | Tier1 dsDNA positive | Tier2 Index>0 | Total Positive | Specificity |
|---|---|---|---|---|---|
| Rheumatoid arthritis | 127 | 6 | 3 | 9 | 93% |
| Scleroderma | 22 | 1 | 4 | 5 | 77% |
| Dermatomyositis | 10 | 0 | 3 | 3 | 70% |
| Vasculitis | 9 | 1 | 3 | 4 | 56% |
| Sjogren's | 13 | 0 | 3 | 3 | 77% |
| Polymyositis | 7 | 0 | 2 | 2 | 71% |
| Weners granulomatosus | 3 | 0 | 0 | 0 | 100% |
| Fibromyalia | 2 | 0 | 0 | 0 | 100% |
| Sjogren + fibromyalia | 1 | 0 | 0 | 0 | 100% |
| All | 194 | 8 | 18 | 26 | 87% |

N = number

Example 7

Contribution of Serological and CB-CAPs to Active Disease

Disease activity was measured at the time of the study visit using the Safety of Estrogens in Lupus Erythematosus National Assessment (SELENA) version of the SLE Disease Activity Index (SLEDAI) in all SLE patients. A total of 41 SLE patients (19.6%) presented with active disease as assessed using a SLEDAI≥6. Patients presenting active disease had elevated levels of ANA, EC4d, BC4d, PC4d and reduced levels of ECR1 ($p<0.003$). ROC analysis indicated that ANA above 90 units (AUC=0.696) was associated with a 4.0 fold (CI95%: 1.8-8.8) higher likelihood of active disease. Similarly, EC4d above 14.8 units (ROC AUC=0.647), BC4d above 71.5 units (ROC AUC=0.645) and PC4d above 6.3 units (ROC AUC=0.720) were associated with a 3.4 fold (CI95%: 1.6-7.0), a 4.3 fold (CI95%: 1.9-9.7) and 5.4 fold (CI95%: 2.4-12.1) greater likelihood of active disease, respectively. Alternatively, ECR1 below 10 net WI (AUC=0.690) were associated with a 4.1 fold (CI95%: 2.0-8.5) higher likelihood of active disease. Moreover, the index score calculated to differentiate SLE from other diseases was significantly higher in SLE patients presenting with active disease than those with non active disease. ROC analysis revealed that a cutoff of 1.36 on the index differentiated SLE patients with active from those with non active disease with a of 90.2% sensitivity and 54% specificity (46% false positives). Multivariate logistic regression indicated that ANA levels, ECR1 and PC4d levels contributed to active disease.

The activity score as the weighed sum of ANA, ECR1 and PC4d (using the estimates from the logistic regression analysis) was −2.05±1.13 in patients with non active disease and −0.67±1.42 in patients with active disease. ROC analysis indicated that an activity score above −1.38 units was 75.6% sensitive and 72.6% specificity at differentiating patients with activity and non active disease (AUC=0.784).

TABLE 47

CBCAPs levels in SLE patients with non-active vs. active disease
A SLEDAI score ≥ 6 differentiated active from non active disease. Results are
expressed as median interquartile range.

|  | Non-active disease N = 168 | Active disease N = 41 | P value |
|---|---|---|---|
| ANA | | | |
| units/L | 86 (33-131) | 125 (98-140) | <0.001 |
| units/L ≥ 90 | 47.3% | 78.0% | <0.001 |
| EC4d | | | |
| Net MFI | 11.3 (7.2-19.5) | 16.3 (11.3-26.0) | 0.003 |
| Net MFI > 14.8 | 33.7% | 63.4% | <0.001 |
| BC4d | | | |
| Net MFI | 66.2 (33.3-127.7) | 117.0 (75.2-188.6) | 0.004 |
| Net MFI > 71.5 | 44.9% | 78.0% | <0.001 |
| PC4d | | | |
| Net MFI | 5.0 (32.4-10.7) | 13.9 (7.3-43.4) | <0.001 |
| Net MFI > 6.3 | 39.6% | 78.0% | <0.001 |
| ECR1 | | | |
| Net MFI | 13.5 (9.2-17.9) | 9.2 (6.7-12.4) | <0.001 |
| Net MFI > 10.2 | 68.0% | 34.1% | <0.001 |
| INDEX DIAGNOSTIC [ANA + EC4d + BC4d + anti-MCV] | | | |
| Index | 1.74 (−0.02-2.92) | 2.85 (1.81-3.63) | <0.001 |
| Index ≥ 0 | 74.4% | 97.5% | <0.001 |
| Index > 1.36 | 46.4% | 90.2% | <0.001 |
| ACTIVITY SCORE [ANA + PC4d + ECR1] | | | |
| Index | −2.03 (−2.83; −1.23) | −0.94 (−1.37; −0.16) | <0.001 |
| Index > 0 | 16.4% | 64.2% | <0.001 |
| Index >− 1.38 | 7.5% | 40.2% | <0.001 |

What is claimed is:

1. A method for treating systemic lupus erythematosus in a human subject in need thereof, wherein the human subject is negative for systemic lupus erythematosus based on a level of double-stranded DNA antibody; the method comprising:
   (a) measuring a level of erythrocyte-bound complement component C4d (EC4d) marker in a blood sample obtained from the patient;
   (b) measuring a level of B-lymphocyte-bound C4d complement component (BC4d) marker in the blood sample;
   (c) measuring a level of anti-nuclear antibody (ANA) in the blood sample;
   (d) determining a systemic lupus erythematosus risk score comprising the steps of:
      (i) log normalizing the level of EC4d to produce a log normalized level of EC4d, and multiplying the log normalized level of EC4d by a predetermined weighting coefficient to produce a weighted score for EC4d;
      (ii) log normalizing the level of BC4d to produce a log normalized level of BC4d, and multiplying the log normalized level of BC4d by a predetermined weighting coefficient to produce a weighted score for BC4d;
      (iii) multiplying the level of ANA by a predetermined weighting coefficient to produce a weighted score for ANA; and
      (iv) summing the weighted score for each of EC4d, BC4d, and ANA, thereby determining the systemic lupus erythematosus risk score; and
   (e) determining that the human subject has systemic lupus erythematosus based on the systemic lupus erythematosus risk score; and
   (f) treating the human subject from step (e) that has systemic lupus erythematosus based on the systemic lupus erythematosus risk score with an effective amount of cyclophosphamide, a corticosteroid, mycophenolate, methotrexate, azathioprine, leflunomide, belimumab, or hydroxychloroquine.

2. The method of claim 1, wherein step (a) comprises measuring the level of EC4d marker by enzyme-linked immunosorbent assay, indirect immunofluorescence, radioimmunoassay, or flow cytometry; and step (b) comprises measuring the level of BC4d marker by enzyme-linked immunosorbent assay, indirect immunofluorescence, radioimmunoassay, or flow cytometry.

3. The method of claim 1, wherein step (c) comprises measuring the level of ANA in the blood sample by enzyme-linked immunosorbent assay, indirect immunofluorescence, radioimmunoassay, or flow cytometry.

4. The method of claim 1, wherein log in steps (d)(1) and (d)(2) is natural log.

5. The method of claim 1, wherein step (d)(iii) comprises multiplying a number associated with a cutoff value for the level of ANA by a predetermined weighting coefficient to produce a weighted score for ANA.

6. The method of claim 1, wherein measuring the level of EC4d marker comprises measuring the level of EC4d on the surface of erythrocytes.

7. The method of claim 1, wherein measuring the level of BC4d marker comprises measuring the level of BC4d on the surface of B lymphocytes.

8. The method of claim 1, wherein the human subject has a level of EC4d marker that is less than 6 standard deviations above the mean EC4d marker among non-lupus patients.

9. The method of claim 1, wherein the human subject has a level of BC4d marker that is less than 6 standard deviations above the mean BC4d marker among non-lupus patients.

* * * * *